United States Patent
Soltero et al.

(10) Patent No.: US 6,867,183 B2
(45) Date of Patent: Mar. 15, 2005

(54) PHARMACEUTICAL COMPOSITIONS OF INSULIN DRUG-OLIGOMER CONJUGATES AND METHODS OF TREATING DISEASES THEREWITH

(75) Inventors: Richard Soltero, Holly Springs, NC (US); Balasingam Radhakrishan, Chapel Hill, NC (US); Nnochiri N. Ekwuribe, Cary, NC (US); Bruce Rehlaender, Chapel Hill, NC (US); Anthony Hickey, Chapel Hill, NC (US); Li Li Bovet, Chapel Hill, NC (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 10/235,381

(22) Filed: Sep. 5, 2002

(65) Prior Publication Data

US 2003/0083232 A1 May 1, 2003

Related U.S. Application Data

(63) Continuation-in-part of application No. 10/075,097, filed on Feb. 13, 2002.
(60) Provisional application No. 60/318,193, filed on Sep. 7, 2001, provisional application No. 60/377,865, filed on May 3, 2002, and provisional application No. 60/269,198, filed on Feb. 15, 2001.

(51) Int. Cl.$^7$ .......................... A61K 38/28; C07K 14/62
(52) U.S. Cl. ............................. 514/3; 514/784; 530/303
(58) Field of Search ................................. 514/3, 4, 784; 514/606; 530/303, 304, 305, 345; 424/450

(56) References Cited

U.S. PATENT DOCUMENTS

| | | |
|---|---|---|
| 3,256,153 A | 6/1966 | Heimlich .................... 424/497 |
| 3,868,356 A | 2/1975 | Smyth ........................ 530/303 |
| 3,919,411 A | 11/1975 | Glass et al. ............... 424/78.27 |
| 3,950,517 A | 4/1976 | Lindsay et al. ................. 514/3 |
| 4,003,792 A | 1/1977 | Mill et al. ................... 530/303 |
| 4,044,196 A | 8/1977 | Huper et al. ................. 526/271 |
| 4,087,390 A | 5/1978 | Shields .................... 525/54.11 |
| 4,093,574 A | 6/1978 | Shields .................... 525/54.11 |
| 4,100,117 A | 7/1978 | Shields .................... 525/54.11 |
| 4,156,719 A | 5/1979 | Sezaki et al. ............... 424/118 |
| 4,179,337 A | 12/1979 | Davis et al. ................. 435/181 |
| 4,223,163 A | 9/1980 | Guilloty ..................... 568/618 |

(List continued on next page.)

FOREIGN PATENT DOCUMENTS

| | | |
|---|---|---|
| DE | 196 32 440 A1 | 2/1998 |
| EP | 0 031 567 | 7/1981 |
| EP | 0511903 | 4/1992 |

(List continued on next page.)

OTHER PUBLICATIONS

Agrawal et al. "Polymethyacrylate-based Microparticulates of Insulin for Oral Delivery: Preparation and In Vitro Dissolution Stability in the Presence of Enzyme Inhibitors" *International Journal of Pharmaceutics* 225:31–39 (2001).

(List continued on next page.)

*Primary Examiner*—Jeffrey Edwin Russel
(74) *Attorney, Agent, or Firm*—William A. Barrett; Moore & Van Allen PLLC

(57) ABSTRACT

Pharmaceutical compositions that include an insulin drug-oligomer conjugate, a fatty acid component, and a bile salt component are described. The insulin drug is covalently coupled to an oligomeric moiety. The fatty acid component and the bile salt component are present in a weight-to-weight ratio of between 1:5 and 5:1. Methods of treating an insulin deficiency in a subject in need of such treatment using such pharmaceutical compositions are also provided, as are methods of providing such pharmaceutical compositions.

133 Claims, 9 Drawing Sheets

U.S. PATENT DOCUMENTS

| | | | | |
|---|---|---|---|---|
| 4,229,438 | A | 10/1980 | Fujino et al. | 514/15 |
| 4,253,998 | A | 3/1981 | Sarantakis | 525/54.11 |
| 4,277,394 | A | 7/1981 | Fujino et al. | 530/330 |
| 4,338,306 | A | 7/1982 | Kitao et al. | 424/178 |
| 4,348,387 | A | 9/1982 | Brownlee et al. | 424/178 |
| 4,410,547 | A | 10/1983 | Ueno et al. | 426/532 |
| 4,469,681 | A | 9/1984 | Brownlee et al. | 424/178 |
| 4,472,382 | A | 9/1984 | Labrie et al. | 424/177 |
| 4,554,101 | A | 11/1985 | Hopp | 514/17 |
| 4,579,730 | A | 4/1986 | Kidron et al. | 424/19 |
| 4,585,754 | A | 4/1986 | Meisner et al. | 514/8 |
| 4,602,043 | A | 7/1986 | Geho | 514/646 |
| 4,622,392 | A | 11/1986 | Hong et al. | 536/26.22 |
| 4,662,872 | A | 5/1987 | Cane | 604/151 |
| 4,684,524 | A | 8/1987 | Eckenhoff et al. | 424/469 |
| 4,698,264 | A | 10/1987 | Steinke | 428/402.2 |
| 4,704,394 | A | 11/1987 | Geho | 514/288 |
| 4,717,566 | A | 1/1988 | Eckenhoff et al. | 424/438 |
| 4,744,976 | A | 5/1988 | Snipes et al. | 424/408 |
| 4,761,287 | A | 8/1988 | Geho | 424/450 |
| 4,772,471 | A | 9/1988 | Vanlerberghe et al. | 424/480 |
| 4,797,288 | A | 1/1989 | Sharma et al. | 424/476 |
| 4,801,575 | A | 1/1989 | Pardridge | 514/4 |
| 4,822,337 | A | 4/1989 | Newhouse et al. | 604/50 |
| 4,839,341 | A | 6/1989 | Massey et al. | 514/4 |
| 4,840,799 | A | 6/1989 | Appelgren et al. | 424/493 |
| 4,849,405 | A | 7/1989 | Ecanow | 514/3 |
| 4,863,896 | A | 9/1989 | Geho et al. | 514/4 |
| 4,917,888 | A | 4/1990 | Katre et al. | 424/85.91 |
| 4,935,246 | A | 6/1990 | Ahrens | 424/490 |
| 4,946,828 | A | 8/1990 | Markussen | 514/3 |
| 4,957,910 | A | 9/1990 | Sutton et al. | 514/182 |
| 4,963,367 | A | 10/1990 | Ecanow | 424/485 |
| 4,963,526 | A | 10/1990 | Ecanow | 514/3 |
| 4,994,439 | A | 2/1991 | Longenecker et al. | 514/3 |
| 5,013,556 | A | 5/1991 | Woodle et al. | 424/450 |
| 5,055,300 | A | 10/1991 | Gupta | 424/409 |
| 5,055,304 | A | 10/1991 | Makino et al. | 424/465 |
| 5,089,261 | A | 2/1992 | Nitecki et al. | 424/85.2 |
| 5,093,198 | A | 3/1992 | Speaker et al. | 428/402.21 |
| 5,099,074 | A | 3/1992 | Mueller et al. | 568/617 |
| 5,122,614 | A | 6/1992 | Zalipsky | 548/520 |
| 5,157,021 | A | 10/1992 | Balschmidt et al. | 514/3 |
| 5,162,430 | A | 11/1992 | Rhee et al. | 525/54.1 |
| 5,164,366 | A | 11/1992 | Balschmidt et al. | 514/3 |
| 5,202,415 | A | 4/1993 | Jonassen et al. | 530/303 |
| 5,206,219 | A | 4/1993 | Desai | 514/3 |
| 5,283,236 | A | 2/1994 | Chiou | 514/2 |
| 5,286,637 | A | 2/1994 | Veronese et al. | 435/183 |
| 5,292,802 | A | 3/1994 | Rhee et al. | 525/54.1 |
| 5,298,410 | A | 3/1994 | Phillips et al. | 435/188 |
| 5,304,473 | A | 4/1994 | Belagaje et al. | 435/69.7 |
| 5,308,889 | A | 5/1994 | Rhee et al. | 523/113 |
| 5,312,808 | A | 5/1994 | Shorr et al. | 514/6 |
| 5,320,094 | A | 6/1994 | Laube et al. | 128/203.12 |
| 5,320,840 | A | 6/1994 | Camble et al. | 424/85.1 |
| 5,321,009 | A | 6/1994 | Baeder et al. | 514/4 |
| 5,324,775 | A | 6/1994 | Rhee et al. | 525/54.2 |
| 5,328,955 | A | 7/1994 | Rhee et al. | 525/54.1 |
| 5,349,052 | A | 9/1994 | Delgado et al. | 530/351 |
| 5,359,030 | A | 10/1994 | Ekwuribe | 530/303 |
| 5,364,838 | A | 11/1994 | Rubsamen | 514/3 |
| 5,405,621 | A | 4/1995 | Sipos | 424/490 |
| 5,405,877 | A | 4/1995 | Greenwald et al. | 514/772.3 |
| 5,413,791 | A | 5/1995 | Rhee et al. | 424/422 |
| 5,415,872 | A | 5/1995 | Sipos | 424/490 |
| 5,420,108 | A | 5/1995 | Shohet | 514/3 |
| 5,428,128 | A | 6/1995 | Mensi-Fattohi et al. | 530/302 |
| 5,438,040 | A | 8/1995 | Ekwuribe | 514/3 |
| 5,444,041 | A | 8/1995 | Owen et al. | 514/2 |
| 5,446,091 | A | 8/1995 | Rhee et al. | 525/54.1 |
| 5,457,066 | A | 10/1995 | Frank et al. | 435/68.1 |
| 5,461,031 | A | 10/1995 | De Felippis | 514/4 |
| 5,468,478 | A | 11/1995 | Saifer et al. | 424/78.27 |
| 5,468,727 | A | 11/1995 | Phillips et al. | 514/12 |
| 5,504,188 | A | 4/1996 | Baker et al. | 530/304 |
| 5,506,203 | A | 4/1996 | Bäckström et al. | 514/4 |
| 5,518,998 | A | 5/1996 | Bäckström et al. | 514/3 |
| 5,523,348 | A | 6/1996 | Rhee et al. | 525/54.1 |
| 5,529,915 | A | 6/1996 | Phillips et al. | 435/188 |
| 5,545,618 | A | 8/1996 | Buckley et al. | 514/12 |
| 5,550,188 | A | 8/1996 | Rhee et al. | 525/54.1 |
| 5,567,422 | A | 10/1996 | Greenwald | 424/78.3 |
| 5,579,797 | A | 12/1996 | Rogers | 135/90 |
| 5,606,038 | A | 2/1997 | Regen | 536/6.5 |
| 5,612,460 | A | 3/1997 | Zalipsky | 530/391.9 |
| 5,631,347 | A | 5/1997 | Baker et al. | 530/303 |
| 5,637,749 | A | 6/1997 | Greenwald | 558/6 |
| 5,643,575 | A | 7/1997 | Martinez et al. | 424/194.1 |
| 5,646,242 | A | 7/1997 | Baker et al. | 530/303 |
| 5,650,388 | A | 7/1997 | Shorr et al. | 514/6 |
| 5,658,878 | A | 8/1997 | Bäckström et al. | 514/3 |
| 5,681,567 | A | 10/1997 | Martinez et al. | 424/178.1 |
| 5,681,811 | A | 10/1997 | Ekwuribe | 514/8 |
| 5,693,609 | A | 12/1997 | Baker et al. | 514/3 |
| 5,693,769 | A | 12/1997 | Kahne et al. | 536/5 |
| 5,700,904 | A | 12/1997 | Baker et al. | 530/305 |
| 5,704,910 | A | 1/1998 | Humes | 604/52 |
| 5,707,648 | A | 1/1998 | Yiv | 424/450 |
| 5,714,519 | A | 2/1998 | Cincotta et al. | 514/616 |
| 5,714,639 | A | 2/1998 | Bowman et al. | 568/620 |
| 5,738,846 | A | 4/1998 | Greenwald et al. | 424/85.7 |
| 5,747,445 | A | 5/1998 | Bäckström et al. | 514/4 |
| 5,747,642 | A | 5/1998 | De Felippis | 530/304 |
| 5,750,497 | A | 5/1998 | Havelund et al. | 514/3 |
| 5,763,396 | A | 6/1998 | Weiner et al. | 514/3 |
| 5,766,620 | A | 6/1998 | Heiber et al. | 424/436 |
| 5,824,638 | A | 10/1998 | Burnside et al. | 514/3 |
| 5,830,853 | A | 11/1998 | Bäckström et al. | 514/4 |
| 5,830,918 | A | 11/1998 | Sportsman et al. | 514/648 |
| 5,843,886 | A | 12/1998 | Weiner et al. | 514/3 |
| 5,849,860 | A | 12/1998 | Hakimi et al. | 528/370 |
| 5,853,748 | A | 12/1998 | New | 424/439 |
| 5,854,208 | A | 12/1998 | Jones et al. | 514/3 |
| 5,856,451 | A | 1/1999 | Olsen et al. | 530/402 |
| 5,866,538 | A | 2/1999 | Norup et al. | 514/3 |
| 5,866,584 | A | 2/1999 | Cincotta et al. | 514/288 |
| 5,874,111 | A | 2/1999 | Maitra et al. | 424/499 |
| 5,889,153 | A | 3/1999 | Suzuki et al. | 530/350 |
| 5,898,028 | A | 4/1999 | Jensen et al. | 514/4 |
| 5,902,588 | A | 5/1999 | Greenwald et al. | 424/278.1 |
| 5,905,140 | A | 5/1999 | Hansen | 530/303 |
| 5,907,030 | A | 5/1999 | Shen et al. | 530/331 |
| 5,922,675 | A | 7/1999 | Baker et al. | 514/4 |
| 5,932,462 | A | 8/1999 | Harris et al. | 435/188 |
| 5,942,248 | A | 8/1999 | Barnwell | 424/457 |
| 5,948,751 | A | 9/1999 | Kimer et al. | 514/4 |
| 5,952,008 | A | 9/1999 | Bäckström et al. | 424/499 |
| 5,952,297 | A | 9/1999 | De Felippis et al. | 514/3 |
| 5,962,267 | A | 10/1999 | Shin et al. | 435/69.4 |
| 5,968,549 | A | 10/1999 | New et al. | 424/450 |
| 5,969,040 | A | 10/1999 | Hallahan et al. | 525/54.1 |
| 5,981,709 | A | 11/1999 | Greenwald et al. | 530/351 |
| 5,985,263 | A | 11/1999 | Lee et al. | 424/85.2 |
| 5,997,848 | A | 12/1999 | Patton et al. | 424/46 |
| 6,004,574 | A | 12/1999 | Bäckström et al. | 424/434 |
| 6,011,008 | A | 1/2000 | Domb et al. | 514/8 |
| 6,025,325 | A | 2/2000 | Campfield et al. | 514/2 |
| 6,034,054 | A | 3/2000 | De Felippis et al. | 514/4 |
| 6,042,822 | A | 3/2000 | Gilbert et al. | 424/85.7 |
| 6,043,214 | A | 3/2000 | Jensen et al. | 514/3 |

| | | | |
|---|---|---|---|
| 6,051,551 A | 4/2000 | Hughes et al. | 514/3 |
| 6,057,292 A | 5/2000 | Cunningham et al. | 514/12 |
| 6,063,761 A | 5/2000 | Jones et al. | 514/3 |
| 6,093,391 A | 7/2000 | Kabanov et al. | 424/85.1 |
| 6,113,906 A | 9/2000 | Greenwald et al. | 424/194.1 |
| 6,147,108 A | 11/2000 | Hauptman | 514/449 |
| 6,165,976 A | 12/2000 | Bäckström et al. | 514/3 |
| 6,177,087 B1 | 1/2001 | Greenwald et al. | 424/278.1 |
| 6,191,105 B1 | 2/2001 | Ekwuribe et al. | 514/3 |
| 6,200,602 B1 | 3/2001 | Watts et al. | 424/463 |
| 6,211,144 B1 | 4/2001 | Havelund | 514/4 |
| 6,248,363 B1 | 6/2001 | Patel et al. | 424/497 |
| 6,251,856 B1 | 6/2001 | Markussen et al. | 514/3 |
| 6,255,502 B1 | 7/2001 | Penkler et al. | 552/549 |
| 6,258,377 B1 | 7/2001 | New et al. | 424/450 |
| 6,268,335 B1 | 7/2001 | Brader | 514/3 |
| 6,306,440 B1 | 10/2001 | Bäckström et al. | 424/499 |
| 6,309,663 B1 | 10/2001 | Patel et al. | 424/450 |
| 6,310,038 B1 | 10/2001 | Havelund | 514/4 |
| 6,323,311 B1 | 11/2001 | Liu et al. | 530/303 |
| 6,335,316 B1 | 1/2002 | Hughes et al. | 514/3 |
| 6,342,225 B1 | 1/2002 | Jones et al. | 424/193.1 |
| 6,506,730 B1 | 1/2003 | Lee et al. | 514/12 |
| 2002/0018811 A1 | 2/2002 | Penteado et al. | 424/474 |
| 2002/0160938 A1 | 10/2002 | Brandenberg et al. | 514/3 |
| 2003/0004304 A1 | 1/2003 | Ekwuribe et al. | 528/425 |
| 2003/0027748 A1 | 2/2003 | Ekwuribe et al. | 514/3 |
| 2003/0027995 A1 | 2/2003 | Ekwuribe et al. | 530/399 |
| 2003/0050228 A1 * | 3/2003 | Ekwuribe et al. | 514/3 |
| 2003/0060606 A1 | 3/2003 | Ekwuribe et al. | 530/399 |
| 2003/0069170 A1 | 4/2003 | Soltero et al. | 514/2 |
| 2003/0083232 A1 | 5/2003 | Soltero et al. | 514/3 |
| 2003/0087808 A1 | 5/2003 | Soltero et al. | 514/3 |
| 2003/0144468 A1 | 7/2003 | Ekwuribe et al. | 528/425 |
| 2004/0038867 A1 * | 2/2004 | Still et al. | 514/3 |

FOREIGN PATENT DOCUMENTS

| | | |
|---|---|---|
| EP | 0483465 B1 | 5/1992 |
| EP | 0 483 465 | 8/1995 |
| EP | 0 597 007 | 10/1996 |
| EP | 0 621 777 | 11/1996 |
| EP | 0 822 218 A2 | 2/1998 |
| EP | 0 797 615 | 1/1999 |
| GB | 1 492 997 | 11/1977 |
| JP | 52067313 A | 5/1977 |
| JP | 01207320 | 8/1989 |
| JP | 1 254 699 | 10/1989 |
| WO | WO 93/01802 | 2/1993 |
| WO | WO 95/09831 | 4/1995 |
| WO | WO 95/30641 | 11/1995 |
| WO | WO 98/07745 | 2/1998 |
| WO | WO 99/32134 | 7/1999 |
| WO | WO 99/65941 | 12/1999 |
| WO | WO 00/078302 A1 | 12/2000 |
| WO | WO 01/12230 | 2/2001 |

OTHER PUBLICATIONS

Allaudeen et al. "Orally Active Insulin: A Single Insulin Conjugate Selected for Future Studies" 60th Annual Meeting of the American Diabetes Assoc., Atlanta, GA, Jun. 2000 (Abstract).

Anderson et al. "HIM2, a Novel Modified Insulin, has Improved Systemic Pharmacokinetics in Normal Dogs, Compared to Unmodified Insulin" American Diabetes Association 62nd Annual Meeting, Jun. 2002 (Abstract).

Aoki et al. "Chronic Intermittent Intravenous Insulin Therapy: A New Frontier in Diabetes Therapy" *Diabetes Technology & Therapeutics* 3(1):111–123 (2001).

Block, Lawrence H. "Pharmaceutical Emulsions and Microemulsions" *Pharmaceutical Dosage Forms: Disperse Systems* vol. 2, Ed. Lieberman et al., pp. 47–109 (1996).

Bone et al., "Successful Treatment of an Insulin Dependent Rat Model of Human Type I Diabetes with Orally Active Insulin" Program and Abstracts, 4th International Workshop on Lessons from Animal Diabetes, Omiya, Japan, Nov. 1994 (Abstract).

Bone et al. "Successful Treatment of Type 1 Diabetes with Orally–Active Insulin: Studies in The Insulin Dependent BB/S Rat" Program and Abstracts, 55th Annual Meeting of the American Diabetes Association, Atlanta Georgia, Jun. 1995 (Abstract).

Brange and Volung "Insulin Analogs with Improved Pharmacokinetic Profiles" *Advanced Drug Delivery Reviews* 35:307–335 (1999).

Cleland et al. "Emerging Protein Delivery Methods" *Current Opinion in Biotechnology* 12:212–219 (2001).

Clement et al., "Effects of Multiple Doses of Orally Administered Hexyl Insulin M2 (HIM2) on Postprandial Blood Glucose (PPG) Concentrations in Type 1 Diabetic (TI) Patients" American Diabetes Association 62nd Annual Meeting, Jun. 2002 (Poster).

Clement et al. "Oral Insulin Product Hexyl–Insulin Monoconjugate 2 (HIM2) in Type 1 Diabetes Mellitus: The Glucose Stabilization Effects of HIM2" *Diabetes Technology & Therapeutics* 4(4):459–466 (2002).

Clement, Stephen "A Dose–Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Abstract).

Clement, Stephen "A Dose–Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Poster).

Damge et al. "Poly(alkyl cyanoacrylate) Nanospheres for Oral Administration of Insulin" *Journal of Pharmaceutical Sciences* 86(12):1403–1409 (Dec. 1997).

Dandona et al., "Effect of an Oral Modified Insulin on Blood Glucose Levels in Fasting and Fed Type 1 Diabetic Patients Receiving a 'Basal' Regimen of Injected Insulin" American Diabetes Association Annual Meeting (Jun. 25, 2001) (Abstract).

Ekwuribe et al. "Oral Insulin Delivery: Hydrolyzable Amphiphilic Oligomer Conjugates Prolong Glucose Reduction" *Proceed Int'l Symp. Control. Rel. Biooact. Mater,* 26:147–148 (1999).

Ekwuribe et al. *Calcitonin Drug–Oligomer Conjugates, and Uses Thereof,* U.S. Appl. No. 10/166,355, filed Nov. 8, 2002, including Preliminary Amendment dated Feb. 26, 2003 and Supplemental Preliminary Amendment dated Mar. 31, 2003.

Ekwuribe et al. *Mixtures of Drug–Oligomer Conjugates Comprising Polyalkylene Glycol, Uses Thereof, and Methods of Making Same,* U.S. Appl. No. 09/873,797, filed Jun. 4, 2001.

Ekwuribe, Nnochiri "Conjugation–Stabilized Polypeptide Compositions, Therapeutic Delivery and Diagnostic Formulations Comprising Same, and Method of Making and Using the Same" *Biotechnology Advances* 14(4):575–576 (1996) (Abstract).

Francis et al. "Polyethylene Glycol Modification: Relevance of Improved Methodology to Tumour Targeting" Journal of Drug Targeting 3:321–340 (1996).

Guzman et al. "Effects of Fatty Ethers and Stearic Acid on the Gastrointestinal Absorption of Insulin" PRHSJ 9(2):155–159 (1990).

Harris, J. Milton "Laboratory Synthesis of Polyethylene Glycol Derivatives" J. Macromol. Science—Rev. Macromol. Chem. Phys. C25(3):325–373 (1985).

Hinds et al. "Synthesis and Characterization of Poly(ethylene glycol)–Insulin Conjugates" Bioconjugate Chem. 11:195–201 (2000).

Hosny et al. "Promotion of Oral Insulin Absorption in Diabetic Rabbits Using pH–Dependent Coated Capsules Containing Sodium Cholate" Pharmaceutica Acta Helvetiae 72:203–207 (1997).

Kipnes et al. "Control of Postprandial Plasma Glucose by an Oral Insulin Product (HIM2) in Patients with Type 2 Diabetes" Emerging Treatments and Technologies 26:2 (2003).

Kipnes et al. "The Effects of an Oral Modified Insuling on Postprandial Blood Glucose Levels in Patients with Type 2 Diabetes" American Diabetes Association Annaul Meeting (Jun. 24, 2001) (Abstract).

Kipnes et al. "The Effects of an Oral Modified Insulin on Postprandial Blood Glucose Levels in Patients with Type 2 Diabetes Mellitus" American Diabetes Association Annual Meeting (Jun. 2001) (Poster).

Kube, D.M. "Multitalented Proteins Play a Key Role in Therapeutics" Genomics and Proteomics (Sep. 2002).

Marschutz et al. "Oral Peptide Drug Delivery: Polymer–Inhibitor Conjugates Protecting Insulin from Enzymatic Degradation In Vitro" Biomaterials 21:1499–1507 (2000).

Mesiha et al. "Hypoglycaemic effect of oral insulin preparations containing Brij 35, 52, 58 or 92 and stearic acid" J. Pharm. Pharmacol. 33:733–734 (1981).

Michael et al. "Loss of Insulin Signaling in Hepatocytes Leads to Severe Insulin Resistance and Progressive Hepatic Dysfunction" Molecular Cell 6:87–97 (1999).

Moghaddam, Amir "Use of polyethylene glycol polymers for bioconjugations and drug development" American Biotechnology Laboratory pp. 42, 44 (Jul. 2001).

Musabayane et al. "Orally Administered, Insulin–Loaded Amidated Pectin Hydrogel Beads Sustain Plasma Concentrations of Insulin in Streptozotocin–Diabetic Rats" Journal of Endocrinology 164:1–6 (2000).

Neubauer et al. "Influence of Polyethylene Glycol Insulin on Lipid Tissues of Experimental Animals" Diabetes 32:953–958 (Oct. 1983).

Pang, David C. "Bridging Gaps in Drug Discovery and Development" Pharmaceutical Technology 22:82–94 (Nov. 1998).

Pauletti et al. "Improvement of Oral Peptide Bioavailability: Peptidomimetics and Prodrug Strategies" Advanced Drug Delivery Reviews 27:235–256 (1997.

Puskas et al. "Investigation of Chymotrypsin Digestion Profile of Orally Active Insulin Conjugate HIM2" Program and Abstracts, 2001 Annual Meeting & Exposition, Amer. Assoc. Pharm. Sci., Denver, CO, Oct. 2001 (Abstract).

Radhakrishnan et al. "Chemical Modification of Insulin with Amphiphilic Polymers Imroves Intestinal Delivery," Proceed. Intl. Symp. Control. Rel. Bioact. Mater. 25:124–125 (1998).

Radhakrishnan et al. "Oral Delivery of Insulin: Single Selective Modification at B29–LYS With Amphiphilic Oligomer" Program and Abstracts, 1999 National Meeting of the Ameri. Assoc. Pharm. Scient., New Orleans, LA (1999) (Abstract).

Rhadhakrishnan et al., Stability and Physical Characteristics of Orally Active Amphiphilic Human Insulin Analog, Methoxy (Polyethylene Glycol) Hexanoyl Human Recombinant Insulin (HIM2), Proceed. Int'l. Symp. Control. Rel. Bioact. Mater., vol. 27 pp. 1038–1039 (2000).

Radhakrishnan et al. "Structure–Activity Relationship of Insulin Modified with Amphiphilic Polymers" Program and Abstracts, 1998 National Meeting of the Amer. Assoc. Pharm. Scient., San Francisco, CA Pharm. Sci. 1(1):S–59 (1998) (Abstract).

Radhakrishnan et al., Insulin Polypeptide–Oligomer Conjugates, Proinsulin Polypeptide–Oligomer Conugates and Methods of Synthesizing Same, U.S. Appl. No. 10/389,499, filed Mar. 17, 2003.

Richards et al. "Self–Association Properties of Monomeric Insulin Analogs Under Formulation Conditions" Pharmaceutical Research 15(9):1434–1441 (1998).

Scott–Moncrieff et al. "Enhancement of Intestinal Insulin Absorption by Bile Salt–Fatty Acid Mixed Micelles in Dogs" Journal of Pharmaceutical Sciences 83(10):1465–1469 (1994).

Shah and Shen "Transcellular Delivery of an Insulin–Transferrin Conjugate in Enterocyte–like Caco–2 Cells" Journal of Pharmaceutical Sciences 85(12):1306–1311 (1996).

Shen et al. "(C) Means to Enhance Penetration; (3) Enhancement of polyptide and protein absorption by macromolecular carriers via endocytosis and transcytosis" Advanced Drug Del. Reviews 8:93–113 (1992).

Sindelar et al. "A Comparison of the Effects of Selective Increases in Peripheral or Portal Insulin on Hepatic Glucose Production in the Conscious Dog"Diebetes 45:1594–1604 (1996).

Sirokman et al. "Refolding and proton pumping activity of a polyethylene glycol–bacteriorhodopsin water–soluble conjugate" Protein Science 12:1161–1170 (1993).

Sluzky et al. "Kinetics of Insulin Aggregation in Aqueous Solutions Upon Agitation in the Presence of Hydrophobic Surfaces" Proc. Natl. Acad. Sci. 88:9377–9381 (Nov. 1991).

Soltero et al. Insulin Polypeptide–Oligomer Conjugates, Proinsulin Polyptide–Oligomer Conjugates and Methods of Synthesizing Same U.S. Appl. No. 10/382,022, filed Mar. 5, 2003.

Soltero et al. Pharmaceutical Compositions of Drug–Oligomer Conjugates and Methods of Treating Diseases Therewith U.S. Appl. No. 10/382,069, filed Mar. 5, 2003.

Soltero et al. Pharmaceutical Compositions of Insulin Drug–Oligomer Conjugates and Methods of Treating Diseases Therewith U.S. Appl. Ser. No. 10/382,155, filed Mar. 5, 2003.

Song et al. "Direct Measurement of Pulsatile Insulin Secretion from the Portal Vein in Human Subjects" Journal of Clinical Endocrinology & Metabolism 85(12):4491–4499 (2000).

Still and McAllister "Effects of Orally Active Modified Insulin in Type 1 Diabetic Patients" Clinical Pharmacol. Therap. 69(2):P95 (Feb. 2001) (Abstract).

Still and McAllister "Effects of Orally Active Modified Insulin in Type I Diabetic Patients" Slide Presentation Annual Meeting of the American Society for Clinical Pharmacology & Therapeutics, Orlando, FL, Mar. 9, 2001.

Still and McAllister "Effects of Orally Active Modified Insulin in Type 1 Diabetic Patients" Annual Meeting of the American Society for Clinical Pharmacology & Therapeutics, Orlando, FL, Mar. 9, 2001 (Handout).

Still et al. "Magnitude and Variability of Pharmacokintic and Glucodynamic Responses to Modified Human Insulin Administered Orally to Healthy Volunteers" *Diabetes Research and Clinical Practice* 56:S77 (2002) (Abstract).

Still et al., *Method of Reducing Hypoglycemic Episodes in the Treatment of Diabetes Mellitus,* U.S. Appl. Ser. No. 10/461,199, filed Jun. 13, 2003.

Still, J. Gordon "Development of Oral Insulin: Progress and Current Status" *Diabetes/Metabolism Research and Reviews* 18(1):S29–S37 (2002).

Still, J. Gordon "Oral Insulin Development" Slide Presentation, VI International St. Barts Symposium Diabetes 2000: Therapy and Technology, London, England, May 12, 2000.

Stocklin et al. "A Stable Isotope Dilution Assay for the In Vivo Determination of Insulin Levels in Humans by Mass Spectrometry" *Diabetes* 46(1):1–7 (Jan. 1997).

Uchio et al. "Site–Specific Insulin Conjugates with Enhanced Stability and Extended Action Profile" *Advanced Drug Delivery Reviews* 35:289–306 (1999).

Vreeland et al. "Molar Mass Profiling of Synthetic Polymers by Free–Solution Capillary Electrophoresis of DNA–Polymer Conjugates" *Analytical Chemistry* 73(8):1795–1803 (2001).

Wei et al. "A Poly(Ethylene Glycol) Water–soluble Conjugate of Porin: Refolding to the Native State" *Biochemistry* 34:648–6415 (1995).

Xia et al. "Effects of polyoxyethylene chain length distribution on the interfacial properties of polyethylene glycol n–dodecyl ether" *Yingyong Huaxue* 2(4): 59–65 (1985) (Abstract).

Zalipsky et al. "Peptide Attachment to Extremities of Liposomal Surfaces Grafted PEG Chains: Preparation of the Long–Circulating Form of Laminin Pentapeptide YIGSR" *Bioconjugate Chem.* 6:705–708 (1995).

Ziv and Bendayan "Intestinal Absorption of Peptides Through the Enterocytes" *Microscopy Research and Technique* 49:346–352 (2000).

International Search Report for International Application No. PCT/US02/28536 dated Sep. 15, 2003.

International Search Report for International Application No. PCT/US02/28429 dated Mar. 14, 2003.

Abuchowski, A. and F. F. Davis, "Soluble Polymer–Enzyme Adducts," pp. 368–383, Enzymes as Drugs, J. S. Holcenberg, John Wiley, 1981.

Akiyama, M. et al., "The Synthesis of New Derivatives of 1–.beta.–D–Arabinofuranosylcytosine," Chem. Pharm. Bull., 1978, 26(3): p. 981–984.

Allcock et al., "Contemporary Polymer Chemistry," 394–403 (2nd. ed., 1991).

Ansell, S. et al., "Application of Oligo–(14–amino–3,6,9, 12–tetraoxatetradecanoic acid) Lipid Conjugates as Steric Barrier Molecules in Liposomal Formulations," Bioconjugate Chem., 10: 653–666 (1999).

Aoshima, M. et al., "N.sup.4 Behenoyl–1–.beta.–D–Arabinofuranosylcytosine as a Potential New Antitumor Agent," Cancer Research, 1977, 37: pp. 2481–2486.

Baker, D. C. et al., "Prodrugs of 9–.beta.–D–Arabinofuranosyladenine. 1. Synthesis and Evaluation of Some 5'–(O–Acyl) Derivatives," J. Med. Chem., 1978, 21(12): pp. 1218–1221.

Banting et al., "Pancreatic Extracts in the Treatment of Diabetes Mellitus: Preliminary Report," Can. Med. Assoc. J., 145(10): 1281–1286 (1991).

Banting, R. G., et al, "Pancreatic Extracts in the Treatment of Diabetes Mellitus," The Canadian Med. Assoc. J. 1992, 12: 141–146.

Baudys et al., "Stabilization and Intestinal Absorption of Human Calcitonin," J. Contr. Rel. Vol. 39, pp. 145–151 (1996).

Baudys, M. et al, "Synthesis and Characterization of Different Glycosylated Derivatives of Insulin" Proceed. Intern. Symp. Cont. Rel. Bioactive. Mater., 1992, 19: 210–211.

Boccu, E. et al., "Pharmacokinetic Properties of Polyethylene Glycol Derivatized Superoxide Dismutase," Pharm. Res. Comm., 1982 14: 113–120.

Brange, J., "Galenics of Insulin: The Physico–Chemical and Pharmaceutical Aspects of Insulin and Insulin Preparations," Novo Research Institute, Denmark, 18–100 (1987).

Brange, J. et al, "Chemical Stability of Insulin. 1. Hydrolytic Degradation During Storage of Pharmaceutical Preparations," Pharm. Res., 1992, 9(6): 715–726.

Brange, J. et al, "Chemical Stability of Insulin. 2. Formation of Higher Molecular Weight Transformation Products During Storage of Pharmaceutical Preparations," Pharm. Res., 1992, 9(6) 727–734.

Chen et al., "Synthesis and Properties of AMA Amphiphiles," J. Org. Chem., 64: 6870–6873 (1999).

Chien, Y. W., Novel Drug Delivery Systems, pp. 6787–679, Marcell Deffer, Inc., New York, N.Y., 1992.

Conradi, R.A., et al., "The Influence of Peptide Structure on Transport Across Caco–2 Cells," Pharm. Res., 1991, 8(12): 1453–1459.

Coombes, A.G.A. et al., "Biodegradable Polymeric Microparticles for Drug Delivery and Vaccine Formulation: the Surface Attachment of Hydrophilic Species Using the Concept of Poly(Ethylene Glycol) Anchoring Segments," Biomaterials, 18: 1153–1161 (1997).

Coudert et al., "A Novel, Unequivocal Synthesis of Polyethylene Glycols," Synthetic Communications, 16(1): 19–26 (1986).

Delgado et al.; "The Uses and Properties of PEG–Linked Proteins" Critical Reviews in Therapeutic Drug Carrier Systems 9:3,4 249–304 (1992).

Engel et al.; "Insulin: Intestinal Absorption as Water–in–Oil–in–Water Emulsions" NATURE 219 856–857 (1968).

Fasano, Alessio, "Innovative strategies for the oral delviery of drugs and peptides" TIBTECH 16 152–157 (1998).

Forst et al., "New Aspects on Biological Activity of C–peptide in IDDM Patients," Exp. Clin. Endocrinol. Diabetes, 106: 270–276 (1998).

Gish, D. T. et al., "Nucleic Acids. 11. Synthesis of 5'–Esters of 1–.beta.–D–Arabinofuranosylcytosine Possessing Antilekemic and Immunosuppressive Activity," J. Med. Chem., 1971, 14(12): pp. 1159–1162.

Gombotz et al., "Biodegradable Polymers for Protein and Peptide Drug Delivery," Bioconjugate Chem., 6: 332–351 (1995).

Harris, J. Milton, "Laboratory Synthesis of Polyethylene Glycol Derivatives," J. Macromol. Science—Rev. Macromol. Chem. Phys., C25(3): 325–373 (1985).

Hashimoto et al., "Synthesis of Palmitoyl Derivatives of Insulin and Their Biological Activities," Pharmaceutical Research, 6(2): 171–176 (1989).

Hostetler, K. Y. et al., "Synthesis and Antiretroviral Activity of Phospholipid Analogs of Azidothymidine and Other Antiviral Nucleosides," The Journal of Biological Chemistry, 1990, 265(11): pp. 6112–6117.

Hong, C. I. et al., "Nucleoside Conjugates. 7. Synthesis and Antitumor Activity of 1–.beta.–D–Arabinofuranosylcytosine Conjugates of Ether Lipids," J. Med. Chem., 1986, 29: pp. 2038–2044.

Igarashi, R. et al., "Biologically Active Peptides Conjugated with Lecithin for DDS" Proceed. Intern. Symp. Cont. Rel. Bioactiv. Mater. 1990, 17 367–368.

Kemmler et al., "On the Nature and Subcellular Localization of the Proinsulin Converting Enzymes," Federation Proceedings, 30(Abstract 924): 1210Abs (1971).

Kemmler et al., "Studies on the Conversion of Proinsulin to Insulin: I. Conversion in Vitro with Trypsin and Carboxypeptidase B," The Journal of Biological Chemistry, 246(22) 6786–6791 (Nov. 25, 1971).

King et al.; "Preparation of Protein Conjugates with Alkoxypolyethylene Glycols" Int. J. Peptide Protein Res. 16 147–155 (1980).

M. Maislos et al, "The Source of the Circulating Aggregate of Insulin in Type 1 Diabetic Patients is Therapeutic Insulin" J. Clin. Invest., 1986, 77: 717–723.

Nucci, et al. "The Therapeutic Value of Poly(ethylen Glycol)—Modified Proteins" Ac. Drug. Del. Rev. 6: 133–151 1991.

Oka, K. et al, "Enhanced Intestinal Absorption of a Hydrophobic Polymer–conjugated Protein Drug, Smancs, in an Oily Formulations" Pharm. Res., 1990, 7 (8): 852–855.

Patel et al. "Oral Administration of Insulin By Encapsulation Within Liposomes" FEBS Lett. 62(1) 60–63 1976.

Price, JC, Polyethlyene Glycol, 355–361, (not dated).

Ratner, R. E. et al, "Persistent Cutaneous Insulin Allergy Resulting from High–Molecular Weight Insulin Aggregates," Diabetes, 1990, 39: 728–733.

Robbins, D. C. et al, "Antibodies to Covalent Aggregates of Insulin in Blood of Insulin–Using Diabetic Patients" Diabetes, 1987, 36: 838–841.

Russell–Jones, G. J. "Vitamin B12 Drug Delivery", Proceed. Intern. Symp. Control. Rel. Bioactive. Mater., 1992, 19: 102–103.

Saffran et al. "A Model for the Study of the Oral Administration of Peptide Hormones" Can J Biochem 57 548–553 1979.

Saffran, M. et al, "A New Approach to the Oral Administration of Insulin and Other Peptide Drugs," Science, 1986, 233: 1081–1084.

Santiago N. et al, "Oral Immunization of Rats with Influenza Virus M Protein (M1) Microspheres," Proceed. Intern. Symp. Cont. Rel. Bioactive. Mater., 1992, 19: 116–117.

Savva et al., "Effect of PEG Homopolymer and Grafted Amphiphilic PEG–Palmityl on the Thermotropic Phase Behavior of 1,2–Dipalmitoyl–SN–Glycero–3–Phosphocholine Bilayer," Journal of Liposome Research, 9(3): 357–365 (1999).

Shichiri et al.; "Enteral Absorption of Water–in–Oil–in–Water Insulin Emulsions in Rabbits" Diabetologia 10 317–321 (1974).

Szleifer, I. et al., "Spontneous Liposomes Formation Induced by Grafted Poly(Ethylene Oxide) Layers: Theoretical Prediction and Experimental Verification," Proceedings of the National Academy of Sciences of the United States of America, 95(3): 1032–1037 (Feb. 3, 1998).

Taniguchi, T. et al, "Synthesis of Acyloyl Lysozyme and Improvement of its Lymphatic Transport Following Small Intestinal Administration in Rats" Proceed. Intern. Symp. Control. Rel. Bioactiv. Mater., 1992, 19: 104–105.

Wahren et al., "Role of C–peptide in Human Physiology," Am. J. Physiol. Endocrinol. Metab., 278: E759–E768 (2000).

Tyle, Praveen, "Iontophoretic Devices for Drug Delivery," Pharma Research, 3:6 318–326 (1986).

Zalipsky, S. et al., "Attachment of Drugs to Polyethylene Glycols," Eur. Polym. J., 1983, 19(12): pp. 1177–1183.

* cited by examiner

1 TIME (min) VS. MEAN PLASMA INSULIN (μU/mL) - BASELINE (n-17)
2 TIME (min) VS. MEAN PLASMA INSULIN (μU/mL) - 0.125 mg/kg (n=40 fasted, n=32 fed)
3 TIME (min) VS. MEAN PLASMA INSULIN (μU/mL) - 0.25 mg/kg (n=40 fasted, n=32 fed)

PHARMACEUTICAL COMPOSITIONS OF INSULIN DRUG-OLIGOMER CONJUGATES AND METHODS OF TREATING DISEASES THEREWITH

RELATED APPLICATION

This application claims the benefit of U.S. Provisional Application No. 60/318,193, filed Sep. 7, 2001 and U.S. Provisional Application No. 60/377,865, filed May 3, 2002, and is a continuation-in-part application of, and claims priority under 35 U.S.C. § 120 to, U.S. application Ser. No. 10/075,097, filed Feb. 13, 2002, pending, which claims the benefit under 35 U.S.C. § 119(e) of U.S. provisional application Ser. No. 60/269,198, filed Feb. 15, 2001, the disclosures of which are incorporated herein by reference in their entireties.

FIELD OF THE INVENTION

The present invention relates to pharmaceutical compositions and methods of treating diseases therewith.

BACKGROUND OF THE INVENTION

The polypeptide insulin is the primary hormone responsible for controlling the transport, utilization and storage of glucose in the body. The β-cells of the pancreatic islets secrete a single chain precursor of insulin, known as proinsulin. Proteolysis of proinsulin results in removal of certain basic amino acids in the proinsulin chain and the connecting or C-peptide and provides the biologically active polypeptide insulin.

The insulin molecule has been highly conserved in evolution and generally consists of two chains of amino acids linked by disulfide bonds. In the natural human, two-chain insulin molecule (mw 5,800 Daltons), the A-chain is composed of 21 amino acid residues and has glycine at the amino terminus; and the B-chain has 30 amino acid residues and phenylalanine at the amino terminus.

Insulin may exist as a monomer or may aggregate into a dimer or a hexamer formed from three of the dimers. Biological activity, i.e., the ability to bind to receptors and stimulate the biological actions of insulin, resides in the monomer.

Diabetes is a biological disorder involving improper carbohydrate metabolism. Diabetes results from insufficient production of or reduced sensitivity to insulin. In persons with diabetes, the normal ability to use glucose is inhibited, thereby increasing blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness.

There are two varieties of diabetes. Type I is insulin-dependent diabetes mellitus, or IDDM. IDDM was formerly referred to as "juvenile onset diabetes." In IDDM, insulin is not secreted by the pancreas and must be provided from an external source. Type II or adult-onset diabetes can ordinarily be controlled by diet, although in some advanced cases insulin is required.

Before the isolation of insulin in the 1920s, most patients died within a short time after onset. Untreated diabetes leads to ketosis, the accumulation of ketones, products of fat breakdown, in the blood. This is followed by the accumulation of acid in the blood (acidosis) with nausea and vomiting. As the toxic products of disordered carbohydrate and fat metabolism continue to build up, the patient goes into a diabetic coma, which leads to death.

The use of insulin as a treatment for diabetes dates to 1922, when Banting et al. ("Pancreatic Extracts in the Treatment of Diabetes Mellitus," *Can. Med. Assoc. J.*, 12:141–146 (1922)) showed that the active extract from the pancreas had therapeutic effects in diabetic dogs. In that same year, treatment of a diabetic patient with pancreatic extracts resulted in a dramatic, life-saving clinical improvement.

Until recently, bovine and porcine insulin were used almost exclusively to treat diabetes in humans. Today, however, numerous variations in insulin between species are known. Each variation differs from natural human insulin in having amino acid substitution(s) at one or more positions in the A- and/or B-chain. Despite these differences, most mammalian insulin has comparable biological activity. The advent of recombinant technology allows commercial scale manufacture of human insulin (e.g., Humulin™ insulin, commercially available from Eli Lilly and Company, Indianapolis, Ind.) or genetically engineered insulin having biological activity comparable to natural human insulin.

Treatment of diabetes typically requires regular injections of insulin. Due to the inconvenience of insulin injections, various approaches have been attempted to formulate insulin for administration by non-injectable routes.

For example, U.S. Pat. No. 4,338,306 to Kitao et al. proposes pharmaceutical compositions for rectal administration of insulin. The pharmaceutical compositions include insulin and fatty acids having 8 to 14 carbon atoms and nontoxic salts thereof.

U.S. Pat. No. 4,579,730 to Kidron et al. proposes pharmaceutical compositions for the oral administration of insulin. The pharmaceutical compositions include insulin, a bile acid or alkali metal salt thereof, the bile acid being selected from the group consisting of cholic acid, chenodeoxycholic acid, taurocholic acid, taurochenodeoxycholic acid, glycocholic acid, glycochenocholic acid, 3β-hydroxy-12-ketocholic acid, 12α-3β-dihydrocholic acid, and ursodesoxycholic acid, and a protease inhibitor. The composition is provided with an enterocoating to assure passage through the stomach and release in the intestine.

U.S. Pat. No. 5,283,236 to Chiou proposes compositions for systemic delivery of insulin through the eyes where the drug passes into the nasolacrimal duct and becomes absorbed into circulation. The composition includes insulin and an enhancing agent. The enhancing agents proposed include, either alone or in combination, surfactants such as polyoxyethylene ethers of fatty acids and bile salts and acids such as cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurodeoxycholate, chenodeoxycholic acid, and ursodeoxycholic acid. The enhancer is present in a concentration ranging from 0.1% to 5% (w/v).

U.S. Pat. No. 5,658,878 to Bäckström et al. proposes a therapeutic preparation for inhalation that includes insulin and a substance which enhances the absorption of insulin in the lower respiratory tract. The enhancer is preferably a sodium salt of a saturated fatty acid of carbon chain length 10 (i.e., sodium caprate), 12 (sodium laurate), or 14 (sodium myristate). Potassium and lysine salts of capric acid are also proposed. Bäckström et al. note that if the carbon chain length is shorter than about 10, the surface activity of the surfactant may be too low, and if the chain length is longer than about 14, decreased solubility of the fatty acid in water limits its usefulness. As an alternative to the proposed fatty acid enhancers, Bäckström et al. propose the use of the following bile salts—sodium ursodeoxycholate, sodium taurocholate, sodium glycocholate, and sodium taurodihydrofusidate.

U.S. Pat. No. 5,853,748 to New proposes enteric-coated compositions for oral administration of insulin. The composition includes insulin, a bile salt or bile acid, and carbonate or bicarbonate ions, which are used to adjust the pH of the gut to a pH of from 7.5 to 9.

U.S. Pat. No. 6,200,602 to Watts et al. proposes drug delivery compositions for colonic delivery of insulin. The drug delivery compositions include insulin, an absorption promoter which (a) includes a mixture of fatty acids having 6 to 16 carbon atoms or a salt thereof and a dispersing agent, or (b) comprises a mixture of mono/diglycerides of medium chain fatty acids and a dispersing agent, and a coating to prevent the release of the insulin and absorption promoter until the tablet, capsule or pellet reaches the proximal colon.

It is desirable to provide pharmaceutical compositions for administration of insulin that may provide improved bioavailability when compared to the conventional compositions described above.

SUMMARY OF THE INVENTION

Pharmaceutical compositions according to embodiments of the present invention use a mixture of bile salts and fatty acids in a particular ratio that appears to provide synergistic effects in the administration of insulin drug-oligomer conjugates that may not be achieved with bile salts or fatty acids alone. For example, in some embodiments of the present invention, using mixtures of bile salts and fatty acids in a particular ratio alters the precipitation characteristics of the bile salt so that the bile salt more readily re-solubilizes if it happens to precipitate out of the pharmaceutical composition (e.g, upon encountering an acidic environment in the gut). As another example, in some embodiments of the present invention, using mixtures of bile salts and fatty acids in a particular ratio lowers the precipitation point of the bile salt in the pharmaceutical composition, providing additional buffering capacity for the pharmaceutical composition.

According to embodiments of the present invention, a pharmaceutical composition includes an insulin drug-oligomer conjugate that includes an insulin drug covalently coupled to an oligomeric moiety, a fatty acid component that includes a fatty acid, and a bile salt component that includes a bile salt. The fatty acid component and the bile salt component are present in a weight-to-weight ratio of between 1:5 and 5:1. The fatty acid component is present in an amount sufficient to lower the precipitation point of the bile salt compared to a precipitation point of the bile salt if the fatty acid component were not present in the pharmaceutical composition. The bile salt component is present in an amount sufficient to lower the solubility point of the fatty acid compared to a solubility point of the fatty acid if the bile salt were not present in the pharmaceutical composition.

According to other embodiments of the present invention, a pharmaceutical composition includes an insulin drug-oligomer conjugate that includes an insulin drug covalently coupled to an oligomeric moiety, a bile salt component comprising a bile salt, and a fatty acid component comprising a fatty acid. The fatty acid component and the bile salt component are present in a weight-to-weight ratio of between 1:5 and 5:1. The fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were not present in the composition.

According to still other embodiments of the present invention, a pharmaceutical composition includes an insulin drug-oligomer conjugate that includes an insulin drug covalently coupled to an oligomeric moiety, between 0.1 and 15% (w/v) of a fatty acid component, and between 0.1 and 15% (w/v) of a bile salt component. The fatty acid component and the bile salt component are present in a weight-to-weight ratio of between 1:5 and 5:1.

According to other embodiments of the present invention, methods of treating an insulin deficiency in a subject in need of such treatment include administering to the subject a pharmaceutical composition according to embodiments of the present invention.

According to still other embodiments of the present invention, a method of providing a pharmaceutical composition includes selecting an amount of a bile salt to include in the composition based on the ability of the bile salt to increase the solubility of a fatty acid component when the composition has a pH of 8.5 or less.

According to yet other embodiments of the present invention, a method of providing a pharmaceutical composition includes selecting an amount of a fatty acid to include in the composition based on the ability of the fatty acid to lower the precipitation point of a bile salt component in the composition to a pH of 5.5 or less.

According to other embodiments of the present invention, a method of providing a pharmaceutical composition includes selecting an amount of a fatty acid to include in the composition based on the ability of the fatty acid to alter the precipitation characteristics of a bile salt component in the composition.

DETAILED DESCRIPTION OF THE PREFERRED EMBODIMENT

Figure 1:
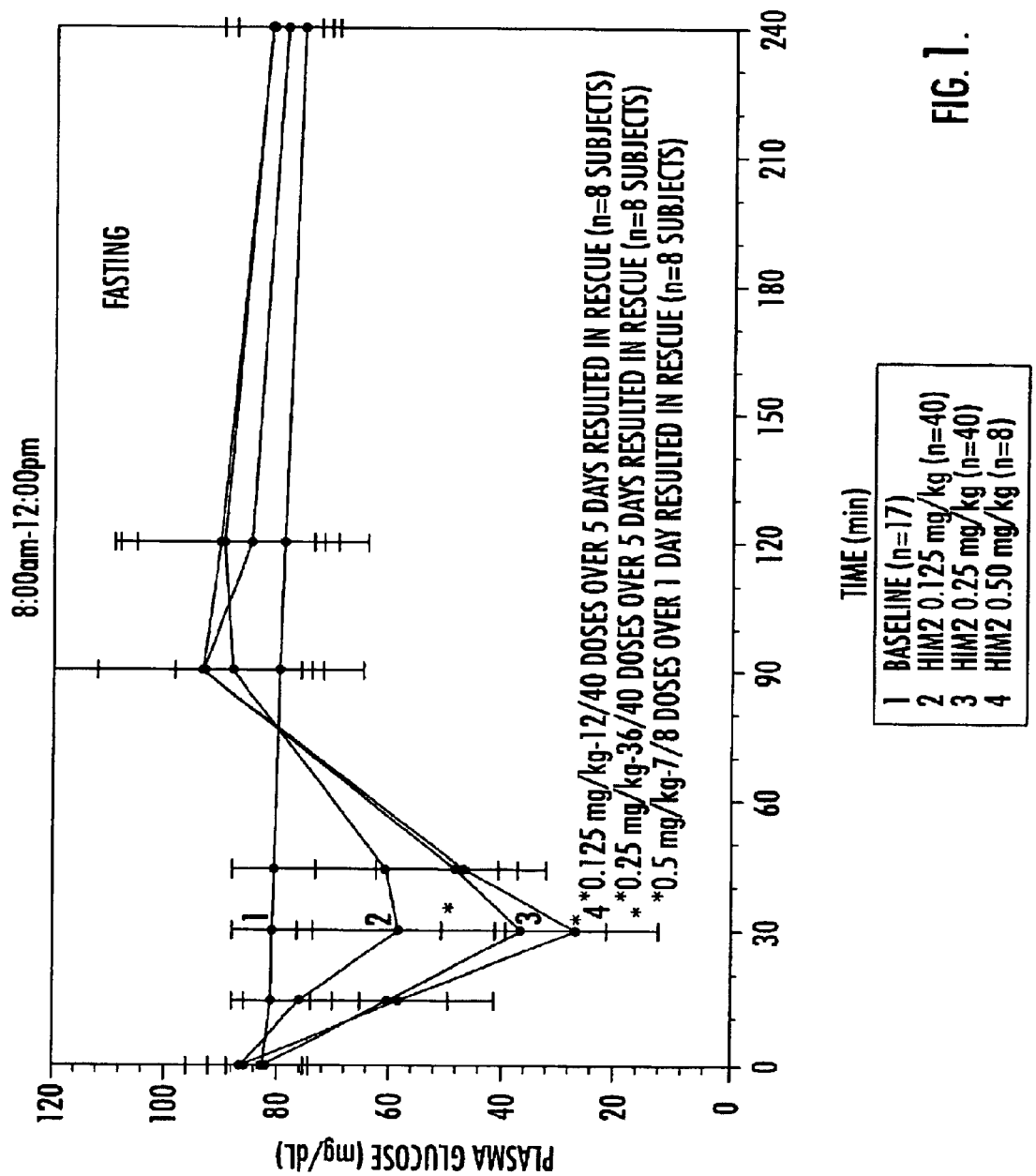
FIG. 1 illustrates a comparison of mean plasma glucose vs. time curves resulting from oral administration of various doses of embodiments of the present invention in fasting, non-diabetic subjects compared with a mean plasma glucose vs. time curve for baseline plasma glucose.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

All amino acid abbreviations used in this disclosure are those accepted by the United States Patent and Trademark Office as set forth in 37 C.F.R. §1.822(b).

As used herein, the term "between" when used to describe various ranges should be interpreted to include the endpoints of the described ranges.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "insulin polypeptide" means a polypeptide possessing at least some of the biological activity of insulin (e.g., ability to affect the body through insulin's primary mechanism of action). For example, an insulin polypeptide may be a polypeptide such as insulin having an A-chain polypeptide and a B-chain polypeptide coupled to the A-chain polypeptide by disulfide bonds. In various embodiments of the present invention, the insulin polypeptide preferably possesses a majority of the biological activity of insulin, more preferably possesses substantially all of the biological activity of insulin, and most preferably possesses all of the biological activity of insulin.

As used herein, the term "insulin" means the insulin of one of the following species human, cow, pig, sheep, horse, dog, chicken, duck, whale, or the like provided by natural, synthetic, or genetically engineered sources. In various embodiments of the present invention, insulin is preferably human insulin.

As used herein, the term "insulin analog" means insulin wherein one or more of the amino acids have been replaced while retaining some or all of the activity of the insulin. The analog is described by noting the replacement amino acids with the position of the replacement as a superscript followed by a description of the insulin. For example, "Pro$^{B29}$ insulin, human" means that the lysine typically found at the B29 position of a human insulin molecule has been replaced with proline.

Insulin analogs may be obtained by various means, as will be understood by those skilled in the art. For example, certain amino acids may be substituted for other amino acids in the insulin structure without eliminating a therapeutically beneficial effect. As the interactive capacity and nature of insulin defines its biological functional activity, certain amino acid sequence substitutions can be made in the amino acid sequence and nevertheless remain a polypeptide without eliminating a therapeutically beneficial effect.

In making such substitutions, the hydropathic index of amino acids may be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids may be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101, the disclosure of which is incorporate herein in its entirety, provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As will be understood by those skilled in the art, insulin analogs may be prepared by a variety of recognized peptide synthesis techniques including, but not limited to, classical (solution) methods, solid phase methods, semi-synthetic methods, and recombinant DNA methods.

Examples of human insulin analogs include, but are not limited to, Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; Ala$^{B28}$ Pro$^{B29}$ insulin, human.

As used herein, the term "insulin fragment" means a segment of the amino acid sequence found in the insulin that retains some or all of the activity of the insulin. Insulin fragments are denoted by stating the position(s) in an amino acid sequence followed by a description of the amino acid. For example, a "B25–B30 human insulin" fragment would be the six amino acid sequence corresponding to the B25, B26, B27, B28, B29 and B30 positions in the human insulin amino acid sequence.

As used herein, the term "insulin fragment analog" means a segment of the amino acid sequence found in the insulin molecule wherein one or more of the amino acids in the segment have been replace while retaining some or all of the activity of the insulin.

As used herein, the term "polypeptide" means a peptide having two or more amino acid residues.

As used herein, the term "amphiphilically balanced" means capable of substantially dissolving in water and capable of penetrating biological membranes.

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—CH$_2$—CH$_2$—O—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

Unless otherwise noted herein, the term "bile salt" includes bile salts and the free acids thereof.

Unless otherwise noted herein, the term "fatty acid" includes fatty acids and pharmaceutically acceptable salts or esters thereof.

As used herein, the term "bile salt component" means a mixture of one or more salts.

As used herein, the term "fatty acid component" means a mixture of one or more fatty acids.

As used herein, the "precipitation point" of a compound or component of the pharmaceutical composition is the pH at which at least 25% of the compound or component precipitates out of the composition. Accordingly, lowering the precipitation point means lowering the pH at which at least 25% of the compound or component precipitates out of the composition. Conversely, raising the precipitation point means raising the pH at which at least 25% of the compound or component precipitates out of the composition.

As used herein, the "solubility point" of a compound or component of the pharmaceutical composition is the pH at which at least 75% of the compound or component is solubilized in the composition. Accordingly, lowering the solubility point means lowering the pH at which at least 75% of the compound or component is solubilized in the composition. Conversely, raising the solubility point means raising the pH at which at least 75% of the compound or component is solubilized in the composition.

As used herein, the term "medium-chain fatty acid" means a saturated or unsaturated fatty acid having from 8 to 14 carbon atoms.

As used herein, the term "long-chain fatty acid" means a saturated or unsaturated fatty acid having greater than 14 carbon atoms.

According to embodiments of the present invention, a pharmaceutical composition comprises an insulin drug-oligomer conjugate, a fatty acid component, and a bile salt component. The insulin drug-oligomer conjugate includes an insulin drug covalently coupled to an oligomeric moiety. The fatty acid component includes a fatty acid, and the bile salt component includes a bile salt.

According to these embodiments of the present invention, the fatty acid component and the bile salt component are present in a weight-to-weight ratio of between 1:5 and 5:1. The fatty acid component and the bile salt component are preferably present in a weight-to-weight ratio of between 1:3 and 3:1 and more preferably present in a weight-to-weight ratio of between 1:2 and 2:1.

According to some embodiments of the present invention, the fatty acid component is present in an amount sufficient to lower the precipitation point of the bile salt compared to a precipitation point of the bile salt if the fatty acid component were not present in the pharmaceutical composition. The fatty acid component is preferably present in an amount sufficient to lower the precipitation point of the bile salt by at least 0.5 pH units, and is more preferably present in an amount sufficient to lower the precipitation point of the bile salt by at least 1.0 pH units.

According to other embodiments of the present invention, the bile salt component is present in an amount sufficient to lower the solubility point of the fatty acid compared to a solubility point of the fatty acid if the bile salt were not present in the pharmaceutical composition. The bile salt component is preferably present in an amount sufficient to lower the solubility point of the fatty acid by at least 0.25 pH units, and is more preferably present in an amount sufficient to lower the solubility point of the fatty acid by at least 0.5 pH units.

According to still other embodiments of the present invention, the fatty acid component is present in an amount sufficient to lower the precipitation point of the bile salt compared to a precipitation point of the bile salt if the fatty acid were not present in the pharmaceutical composition as described above, and the bile salt component is present in an amount sufficient to lower the solubility point of the fatty acid compared to a solubility point of the fatty acid if the bile salt were not present in the pharmaceutical composition as described above.

The bile salt in the bile salt component may be various bile salts as will be understood by those skilled in the art including unconjugated and conjugated bile salts. Unconjugated bile salts are bile salts in which the primary side chain has a single carboxyl group which is at the terminal position and which is unsubstituted. Exemplary unconjugated bile salts include, but are not limited to, cholate, ursodeoxycholate, chenodeoxycholate, and deoxycholate. Conjugated bile salts are bile salts in which the primary side chain has a carboxyl group which is substituted with, for example, an amino acid derivative linked via its nitrogen atom to the carboxyl group. Exemplary conjugated bile salts include, but are not limited to, taurocholate, glycocholate, taurodeoxycholate, and glycodeoxycholate. Mixtures of the various unconjugated and/or conjugated bile salts may also be used. The bile salt is preferably a pharmaceutically acceptable salt of cholic acid. More preferably, the bile salt is sodium cholate. Still more preferably, the bile salt component consists essentially of sodium cholate.

The fatty acid in the fatty acid component may be various fatty acids as will be understood by those skilled in the art including natural and synthetic fatty acids. The fatty acid preferably has between a lower limit of 2, 3, 4, 5, 6, 7, 8, 9, 10, 11, 12, 13, 14, 15, 16, 17, 18, or 19 carbon atoms and an upper limit of 3, 4, 5, 6, 7, 8, 9, 10, 11, 12, 13, 14, 15, 16, 17, 18, 19, 20, 21 or 22 carbon atoms. The fatty acid may be either saturated or unsaturated. Exemplary saturated fatty acids include, but are not limited to, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, one or more of which may be referred to by their common names such as acetic acid, caproic acid, caprylic acid, capric acid, lauric acid, myristic acid, palmitic acid, stearic acid, arachidic acid, behenic acid, lignoceric acid, and cerotic acid. Exemplary unsaturated fatty acids include, but are not limited to, cis-9-octadecenoic acid, trans-9-octadecenoic acid, 9,12-octadecatrienoic acid, 9,12,15-octadecenoic acid, and 5,8,11,14-eicosatetraenoic acid, one or more of which may be referred to by their common names such as oleic acid, elaidic acid, linoleic acid, linolenic acid, and arachidonic acid.

In some embodiments, the fatty acid component comprises a mixture of two or more fatty acids. In other embodiments, the fatty acid component comprises a medium-chain fatty acid and a long-chain fatty acid. The medium-chain fatty acid is preferably capric acid, lauric acid, or a mixture thereof. The long-chain fatty acid is preferably oleic acid.

The insulin drug may be various insulin drugs as will be understood by those skilled in the art. The insulin drug is preferably an insulin polypeptide. The insulin polypeptide preferably has an A-chain polypeptide and a B-chain polypeptide. The A-chain polypeptide is preferably devoid of lysine residues. The B-chain polypeptide preferably comprises a single lysine residue. The A-chain polypeptide and the B-chain polypeptide are preferably cross-linked, and are more preferably cross-linked using one or more disulfide bonds. Still more preferably, the A-chain polypeptide and the B-chain polypeptide each comprise cysteine residues, one or more of which are coupled using one or more disulfide bonds to cross-link the A-chain polypeptide with the B-chain polypeptide. Preferably, the insulin polypeptide is insulin, an insulin analog, an insulin fragment, or an insulin analog fragment. More preferably, the insulin polypeptide is human insulin, a human insulin analog, a human insulin fragment, or a human insulin analog fragment.

The oligomer may be various oligomers as will be understood by those skilled in the art. In general, the oligomer may be any oligomer capable of being coupled to a polypeptide as will be understood by those skilled in the art. For example, the oligomer may be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al., the disclosures of each of which are incorporated herein by reference in their entireties. As another example, the oligomer may be a non-polydispersed oligomer as described in U.S. patent application Ser. No. 09/873,731 filed Jun. 4, 2001 by Ekwuribe et al., entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same," the disclosures of each of which are incorporated herein by reference in their entireties.

In some embodiments, the oligomer comprises a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety is preferably a polyalkylene glycol moiety. The polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 polyalkylene glycol subunits and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 polyalkylene glycol subunits and an upper limit of 5, 6, 7, 8, 9, 10, 11, 12, 13, 14, 15, 16, 17, 18, 19, or 20 polyalkyleneglycol subunits. Even more preferably, the polyalkylene glycol moiety has between a lower limit of 3, 4, 5, or 6 polyalkylene glycol subunits and an upper limit of 5, 6, 7, 8, 9, 10, 11, or 12 polyalkylene glycol subunits. The polyalkylene glycol moiety still more preferably has between a lower limit of 4, 5, or 6 polyalkylene glycol subunits and an upper limit of 6, 7, or 8 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

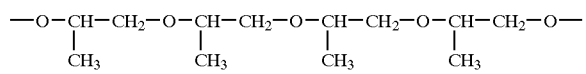

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

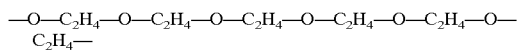

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

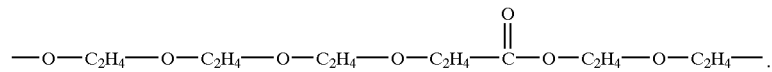

is a polyethylene glycol moiety having four polyethylene glycol subunits and an additional hydrophilic moiety having two polyethylene glycol subunits. Preferably, oligomers according to embodiments of the present invention comprise a polyalkylene glycol moiety and no additional hydrophilic moieties.

The oligomer preferably further comprises one or more lipophilic moieties as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, 20, 21, 22, 23, 24, 25, 26, 27, 28, or 29 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 carbon atoms and an upper limit of 4, 5, 6, 7, 8, 9, 10, 11, 12, 13, 14, 15, 16, 17, 18, 19, 20, 21, or 22 carbon atoms. The lipophilic moiety even more preferably has between a lower limit of 3, 4, 5, 6, 7, 8, or 9 carbon atoms and an upper limit of 4, 5, 6, 7, 8, 9, 10, 11, 12, 13, or 14 carbon atoms. The lipophilic moiety still more preferably has between a lower limit of 3, 4, 5, 6, or 7 carbon atoms and an upper limit of 6, 7, 8, 9, or 10 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate. The fatty acid moiety can be natural or synthetic.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the insulin polypeptide, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

The oligomer may further comprise one or more linker moieties that are used to couple the oligomer with the insulin polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 carbon atoms and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may be a natural or synthetic fatty acid. The fatty acid linker moiety may have between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 carbon atoms and 8, 10, 12, 14 or 16 carbon atoms. When the linker moiety is a fatty acid, the oligomeric moiety is preferably coupled to the insulin drug via the carbonyl group of a carboxylic acid moiety of the fatty acid.

The oligomer may further comprise one or more terminating moieties at the one or more ends of the oligomer, which are not coupled to the insulin polypeptide. The terminating moiety is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 carbon atoms and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 carbon atoms and an upper limit of 5, 6, 7, 8, 9, 10, 11, 12, 13, or 14 carbon atoms. The alkyl or alkoxy moiety even more preferably has between a lower limit of 1, 2, 3, 4, or 5 carbon atoms and an upper limit of 5, 6, 7, 8, 9, or 10 carbon atoms. The alkyl or alkoxy moiety still more preferably has between a lower limit of 1, 2, 3, or 4 carbon atoms and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methylpentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methylpentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to embodiments of the present invention, the insulin drug-oligomer conjugate comprises the structure of Formula I:

$$\text{Insulin drug } -B-L_j-G_k-R-G'_m-R'-G''_n-T \quad (I)$$

wherein:

Insulin drug is a drug which is similar to those described above;

B is a bonding moiety;

L is a linker moiety;

G, G' and G'' are individually selected spacer moieties;

R is a lipophilic moiety and R' is a polyalkylene glycol moiety, or R' is the lipophilic moiety and R is the polyalkylene glycol moiety;

T is a terminating moiety; and j, k, m and n are individually 0 or 1.

The bonding moiety is preferably selected from the group consisting of an ester moity, a thio-ester moiety, an ether moiety, a carbamate moiety, a thio-carbamate moiety, a carbonate moiety, a thio-carbonate moiety, an amide moiety, a urea moiety, and a covalent bond. The linker moiety, spacer moieties, lipophilic moiety, polyalkylene glycol moiety, and terminating moiety are similar to those described above. Preferably, oligomers of these embodiments do not include spacer moieties (i.e., k, m and n are preferably 0).

In other embodiments, the insulin drug-oligomer conjugate comprises the structure of Formula II:

$$\text{Insulin drug } -X(CH_2)_m Y(C_2H_4O)_n R \quad (II)$$

wherein:

Insulin drug is a drug which is similar to those described above;

X is $-C(O)-$ or $-O-$;

Y is an ester, an ether, a carbamate, a carbonate, or an amide bonding moiety, and is preferably an ether bonding moiety;

m is between a lower limit of 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is a terminating moiety similar to those described above.

In still other embodiments, the insulin drug-oligomer conjugate comprises the structure of Formula III:

$$\text{Insulin drug } -X_1-(CH_2)_m(OC_2H_4)_n OR \quad (III)$$

wherein:
Insulin drug is a drug which is similar to those described above;

$X_1$ is —C(O)— or —O—;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 2, 3, 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is a terminating moiety similar to those described above.

In yet other embodiments, the insulin drug-oligomer conjugate comprises the structure of Formula IV:

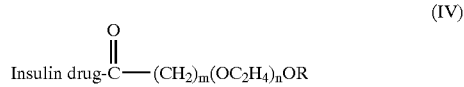

(IV)

wherein:
Insulin drug is a drug which is similar to those described above;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, and is still more preferably between a lower limit of 4, 5, or 6 and an upper limit of 6, 7, or 8 polyalkylene glycol subunits; and R is a terminating moiety similar to those described above.

In still other embodiments, the insulin drug-oligomer conjugate comprises the structure of Formula V:

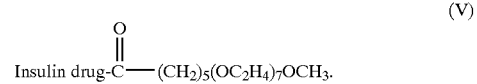

(V)

wherein the insulin drug is a drug which is similar to those described above. When the insulin drug is a human insulin and the conjugate of Formula V consists of the single oligomer coupled to the Lysine at the B29 position of the human insulin, the insulin-oligomer conjugate is referred to as HIM2.

In still other embodiments of the present invention, the drug-oligomer conjugate comprises the structure of Formula VI:

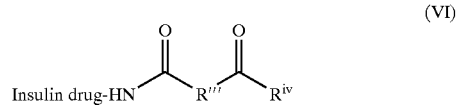

(VI)

wherein:
Insulin drug is a drug which is similar to those described above;

$R'''$ is a hydrophilic moiety; preferably a polyalkylene glycol moiety; more preferably a lower polyalkylene glycol moiety; and still more preferably a polyethylene glycol moiety or polypropylene glycol moiety, where the polyalkylene glycol moiety has at least 1, 2, or 3 polyalkylene glycol subunits; and $R^{iv}$ is a lipophilic moiety; preferably an alkyl moiety having between 1 and 24 carbon atoms; more preferably a lower alkyl moiety; or $R^{iv}$ is a hydrophilic moiety; preferably a polyalkylene glycol moiety; more preferably a lower polyalkylene glycol moiety; and still more preferably a polyethylene glycol moiety or polypropylene glycol moiety, where the polyalkylene glycol moiety has at least 1, 2, or 3 polyalkylene glycol subunits; and $R'''$ is a lipophilic moiety; preferably an alkyl moiety having between 1 and 24 carbon atoms; more preferably a lower alkyl moiety; or When the drug portion of the drug-oligomer conjugate of Formula VI is human insulin, $R'''$ is preferably polyethylene glycol having between a lower limit of 1, 2, 3, 4, 5, 6, or 7 polyethylene glycol subunits and an upper limit of 2, 3, 4, 5, 6, 7, 8, 9, or 10 polyethylene glycol subunits or $R'''$ is polypropylene glycol having between a lower limit of 1, 2, 3, 4, 5, 6, or 7 polypropylene glycol subunits and an upper limit of 2, 3, 4, 5, 6, 7, 8, 9, or 10 polypropylene glycol subunits, and $R^{iv}$ is preferably alkyl having 1, 2, 3, 4, 5, 6, 7, 8, 9, 10, 11, 12, 13, 14, 15, 16, 17, 18, 19, or 20 carbon atoms. More preferably, $R'''$ is polyethylene glycol having between a lower limit of 1, 2, 3, or 4 polyethylene glycol subunits and an upper limit of 2, 3, 4, 5, 6, or 7 polyethylene glycol subunits or $R'''$ is polypropylene glycol having between a lower limit of 1, 2, 3, or 4 polypropylene glycol subunits and an upper limit of 2, 3, 4, 5, 6, or 7 polypropylene glycol subunits, and $R^{iv}$ is alkyl having 1, 2, 3, 4, 5, 6, 7, 8, 9, or 10 carbon atoms. Still more preferably, $R'''$ is polyethylene glycol having between a lower limit of 1, 2, or 3 polyethylene glycol subunits and an upper limit of 3, 4, or 5 polyethylene glycol subunits or $R'''$ is polypropylene glycol having between a lower limit of 1, 2, or 3 polypropylene glycol subunits and an upper limit of 3, 4, or 5 polypropylene glycol subunits, and $R^{iv}$ is alkyl having 3, 4, 5, or 6 carbon atoms.

In yet other embodiments of the present invention, the insulin drug-oligomer conjugate comprises the structure of Formula VII:

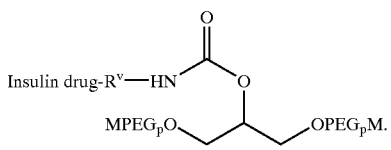

(VII)

wherein:

Insulin drug is a drug which is similar to those described above;

$R^v$ is an alkyl or a fatty acid moiety as described above with reference to the lipophilic moiety; and p is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably between a lower limit of 3, 4, 5, 6, or 7 and an upper limit of 6, 7, 8, 9, or 10.

In the various embodiments described above, the oligomer is covalently coupled to the insulin drug. In some embodiments, the oligomer is coupled to the insulin drug utilizing a hydrolyzable bond (e.g., an ester or carbonate bond). A hydrolyzable coupling may provide an insulin drug-oligomer conjugate that acts as a prodrug. In certain instances, for example where the insulin drug-oligomer conjugate is biologically inactive (i.e., the conjugate lacks the ability to affect the body through the insulin polypeptide's primary mechanism of action), a hydrolyzable coupling may provide for a time-release or controlled-release effect, providing the biologically active insulin drug over a given time period as one or more oligomers are cleaved from their respective biologically inactive insulin drug-oligomer conjugates to provide the biologically active insulin drug. In other embodiments, the oligomer is coupled to the insulin drug utilizing a non-hydrolyzable bond (e.g., a carbamate, amide, or ether bond). Use of a non-hydrolyzable bond may be preferable when it is desirable to allow the biologically inactive insulin drug-oligomer conjugate to circulate in the bloodstream for an extended period of time, preferably at least 2 hours.

Oligomers employed in the various embodiments described above are commercially available or may be synthesized by various methods as will be understood by those skilled in the art. For example, polydispersed oligomers may be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers may be synthesized by methods provided in one or more of the following references: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention are preferably substantially monodispersed and are more preferably monodispersed. Exemplary methods for synthesizing preferred monodispersed oligomers are provided in Examples 1 through 10 below.

In the various embodiments described above, more than one oligomer (i.e., a plurality of oligomers) may be coupled to the insulin drug. The oligomers in the plurality are preferably the same. However, it is to be understood that the oligomers in the plurality may be different from one another, or, alternatively, some of the oligomers in the plurality may be the same and some may be different. When a plurality of oligomers are coupled to the insulin drug, it may be preferable to couple one or more of the oligomers to the insulin drug with hydrolyzable bonds and couple one or more of the oligomers to the insulin drug with non-hydrolyzable bonds. Alternatively, all of the bonds coupling the plurality of oligomers to the insulin drug may be hydrolyzable, but have varying degrees of hydrolyzability such that, for example, one or more of the oligomers is rapidly removed from the insulin drug by hydrolysis in the body and one or more of the oligomers is slowly removed from the insulin drug by hydrolysis in the body.

The oligomer may be coupled to the insulin drug at various nucleophilic residues of the insulin drug including, but not limited to, nucleophilic hydroxyl functions and/or amino functions. When the insulin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-termini of the insulin polypeptide, the coupling preferably forms a secondary amine. When the insulin drug is human insulin, for example, the oligomer may be coupled to an amino functionality of the insulin, including the amino functionality of $Gly^{A1}$, the amino functionality of $Phe^{B1}$, and the amino functionality of $Lys^{B29}$. When one oligomer is coupled to the human insulin, the oligomer is preferably coupled to the amino functionality of $Lys^{B29}$. When two oligomers are coupled to the human insulin, the oligomers are preferably coupled to the amino functionality of $Phe^{B1}$ and the amino functionality of $Lys^{B29}$. While more than one oligomer may be coupled to the human insulin, a higher activity (improved glucose lowering ability) is observed for the mono-conjugated human insulin. Monoconjugates (i.e., when one oligomer is coupled to the insulin drug) are preferably prepared using methods described in U.S. patent application Ser. No. 10/036,744, entitled "Methods of Synthesizing Insulin Polypeptide-Oligomer Conjugates, and Proinsulin Polypeptide-Oligomer Conjugates and Methods of Synthesizing Same," the disclosure of which is incorporated herein by reference in its entirety.

According to other embodiments of the present invention, a pharmaceutical composition comprises an insulin drug-oligomer conjugate, a fatty acid component, and a bile salt component. The insulin drug-oligomer conjugate includes an insulin drug covalently coupled to an oligomeric moiety. The fatty acid component includes a fatty acid, and the bile salt component includes a bile salt.

The insulin drug-oligomer conjugate includes an insulin drug covalently coupled to an oligomeric moiety, and is similar to the insulin drug-oligomer conjugates described above. The fatty acid component and the bile salt component are present in a weight-to-weight ratio of between 1:5 and 5:1, and are preferably present in a weight-to-weight ratio of between 1:3 and 3:1 and more preferably present in a weight-to-weight ratio of between 1:2 and 2:1. The fatty acid component is similar to the fatty acid components described above, and the bile salt component is similar to the bile salt components described above.

According to these embodiments of the present invention, the fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were not present in the composition. The precipitation point of the bile salt in the formulation is preferably at or below a pH of 6.0, and is more preferably at or below a pH of 5.5. The pH above the precipitation point may be various pH's above the precipitation point. In some embodiments, the pH above the precipitation point is at least 0.5 pH units above the precipitation point. In other embodiments, the pH above the precipitation point is at least 0.8 pH units above the precipitation point.

In some embodiments, the first bile salt particles have an average diameter of less than 500 microns and the second bile salt particles have an average diameter of greater than 550 microns. In other embodiments, the first bile salt particles have an average diameter of less than 100 microns and the second bile salt particles have an average diameter of greater than 150 microns.

In some embodiments, the first bile salt particles are able to re-solubilize in less than 75% of the time it would have taken for the second bile salt particles to re-solubilize. In other embodiments, the first bile salt particles are able to re-solubilize in less than half the time it would have taken for the second bile salt particles to re-solubilize.

According to still other embodiments of the present invention, a pharmaceutical composition comprises an insulin drug-oligomer conjugate, between 0.1 and 15% (w/v) of a fatty acid component, and between 0.1 and 15% (w/v) of a bile salt component.

The insulin drug-oligomer conjugate includes an insulin drug covalently coupled to an oligomeric moiety, and is similar to the insulin drug-oligomer conjugates described above. The fatty acid component and the bile salt component are present in a weight-to-weight ratio of between 1:3 and 3:1, and are preferably present in a weight-to-weight ratio of between 1:2 and 2:1. The fatty acid component is similar to the fatty acid components described above, and the bile salt component is similar to the bile salt components described above.

According to these embodiments of the present invention, the concentration of the fatty acid component is between a lower limit of 0.1, 0.2, 0.3, 0.4, 0.5, 0.6, 0.7, 0.8, 0.9, 1, 2, 3, 4, 5, 6, 7, 8, 9, 10, 11, 12, 13, or 14% (w/v) and an upper limit of 0.2, 0.3, 0.4, 0.5, 0.6, 0.7, 0.8, 0.9, 1, 2, 3, 4, 5, 6, 7, 8, 9, 10, 11, 12, 13, 14, or 15% (w/v). The concentration of the fatty acid component is preferably between 0.5 and 10% (w/v), is more preferably between 0.5 and 5% (w/v), and is still more preferably between 1 and 3% (w/v).

According to these embodiments of the present invention, the concentration of the bile acid component is between a lower limit of 0.1, 0.2, 0.3, 0.4, 0.5, 0.6, 0.7, 0.8, 0.9, 1, 2, 3, 4, 5, 6, 7, 8, 9, 10, 11, 12, 13, or 14% (w/v) and an upper limit of 0.2, 0.3, 0.4, 0.5, 0.6, 0.7, 0.8, 0.9, 1, 2, 3, 4, 5, 6, 7, 8, 9, 10, 11, 12, 13, 14, or 15% (w/v). The concentration of the bile salt component is preferably between 0.5 and 10% (w/v), is more preferably between 1 and 5% (w/v), and is still more preferably between 2 and 4% (w/v).

Pharmaceutical compositions according to the present invention may further comprise a buffering component. The buffering component may comprise various buffering agents as will be understood by those skilled in the art. Exemplary buffering agents include, but are not limited to, inorganic acids (e.g., phosphoric acid), organic acids (e.g., citric acid), organic bases (e.g., tris-base (tris(hydroxymethyl) aminomethane), trolamine (triethanolamine), or histadine), and mixtures thereof. The buffering component preferably comprises an organic base, and more preferably comprises tris-base, trolamine, or a mixture thereof. In some embodiments, the buffering component comprises an organic acid and an organic base, and preferably comprises citric acid and tris-base, trolamine, or a mixture thereof. The buffering agent is preferably present in an amount that will buffer the pharmaceutical composition against the acidic environment that may be experienced in the gut as will be understood by one skilled in the art.

In addition to the bile salt component and fatty acid component, pharmaceutical compositions according to embodiments of the present invention may include various suitable excipients as will be understood by those skilled in the art, such as those found in the *National Formulary* 19, pages 2404–2406 (2000), the disclosure of pages 2404 to 2406 being incorporated herein in their entirety. For example, the pharmaceutical compositions may include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, and inert fillers may also be used. Examples of polyols include, but are not limited to, mannitol, sorbitol, xylitol, sucrose, maltose, glucose, lactose, dextrose, and the like. Other inert fillers which may be used encompass those which are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

The pharmaceutical compositions according to embodiments of the present invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular insulin drug-oligomer conjugate which is being used.

Pharmaceutical compositions suitable for oral administration may be presented in discrete units, such as capsules, cachets, lozenges, or tables, each containing a predetermined amount of the insulin drug-oligomer conjugates; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the insulin drug-oligomer conjugate, the fatty acid component, the bile salt component, and a suitable carrier (which may contain one or more accessory ingredients as noted above). In general, the pharmaceutical composition according to embodiments of the present invention are prepared by uniformly and intimately admixing the insulin drug-oligomer conjugate, the fatty acid component, and the bile salt component with a liquid or finely divided solid carrier, or both, and then, if necessary, shaping the resulting mixture.

In some embodiments of the present invention, the pharmaceutical composition is a liquid pharmaceutical composition suitable for oral administration. When the pharmaceutical composition is a liquid pharmaceutical composition, the composition preferably includes a buffering agent as described above. Liquid pharmaceutical compositions according to embodiments of the present invention have a pH that is physiologically compatible. Preferably, liquid pharmaceutical compositions according to embodiments of the present invention have a pH that is between 6.2 and 9.0. In some embodiments, liquid pharmaceutical compositions according to embodiments of the present invention have a pH that is between a lower limit of 6.3, 6.4, 6.5, 6.6, 6.7, 6.8, 6.9, 7.0, 7.1, 7.2, 7.3, 7.4, 7.5, 7.6, or 7.7 and an upper limit of 7.9, 8.0, 8.1, 8.2, 8.3, 8.4, 8.5, 8.6, 8.7, 8.8, or 8.9. In some embodiments, liquid pharmaceutical compositions according to embodiments of the present invention have a pH that is between 7.0 and 8.5. In other embodiments, liquid pharmaceutical compositions according to embodiments of the present invention have a pH that is between 7.4 and 8.2.

In other embodiments of the present invention, the pharmaceutical composition is a solid pharmaceutical composition suitable for oral administration. The solid pharmaceutical composition may be prepared by various methods as will be understood by those skilled in the art. For example, a tablet may be prepared by compressing or molding a powder or granules containing the insulin drug-oligomer conjugate, the fatty acid component, the bile salt component, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions suitable for buccal (sublingual) administration include lozenges comprising the insulin drug-oligomer conjugate, the fatty acid component, and the bile salt component in a flavored base, usually an artificial sweetener and acacia or tragacanth; and pastilles comprising the insulin drug-oligomer conjugate, the fatty acid component, and the bile salt component in an inert base such as gelatin and glycerin or sucrose and acacia.

Pharmaceutical compositions according to embodiments of the present invention suitable for parenteral administration comprise sterile aqueous and non-aqueous injection solutions comprising the insulin drug-oligomer conjugate, the fatty acid component, and the bile salt component, which preparations are preferably isotonic with the blood of the intended recipient. These preparations may contain antioxidants, buffers, bacteriostats and solutes which render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, an injectable, stable, sterile composition comprising the insulin drug-oligomer conjugate, the fatty acid component, and the bile salt component in a unit dosage form in a sealed container may be provided. The mixture of the insulin drug-oligomer conjugate, the fatty acid component, and the bile salt component is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the insulin drug-oligomer conjugate. When the insulin drug-oligomer conjugate is substantially water-insoluble, a sufficient amount of emulsifying agent which is physiologically acceptable may be employed in sufficient quantity to emulsify the insulin drug-oligomer conjugate in an aqueous carrier. One such useful emulsifying agent is phosphatidyl choline.

Pharmaceutical compositions suitable for rectal administration are preferably presented as unit dose suppositories. These may be prepared by admixing the insulin drug-oligomer conjugate, the fatty acid component, and the bile salt component with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the insulin drug-oligomer conjugate, the fatty acid component, and the bile salt component. Suitable formulations comprise citrate or bis\tris buffer (pH 6) or ethanol/water and contain from 0.1 to 0.2M active ingredient.

Methods of treating an insulin deficiency in a subject in need of such treatment by administering any of the various pharmaceutical compositions described above that contain a therapeutically effective amount of the insulin drug-oligomer conjugate are also provided. The effective amount of the insulin drug-oligomer conjugate, the use of which is in the scope of present invention, will vary somewhat from conjugate to conjugate, and subject to subject, and will depend upon factors such as the age and condition of the subject and the route of delivery. Such dosages can be determined in accordance with routine pharmacological procedures known to those skilled in the art. As a general proposition, a dosage from about 0.1 to about 50 mg/kg will have therapeutic efficacy, with all weights being calculated based upon the weight of the insulin drug-oligomer conjugate. Toxicity concerns at the higher level may restrict intravenous dosages to a lower level such as up to about 10 mg/kg, with all weights being calculated based upon the weight of the active base. A dosage from about 10 mg/kg to about 50 mg/kg may be employed for oral administration. Typically, a dosage from about 0.5 mg/kg to 5 mg/kg may be employed for intramuscular injection. The frequency of administration is usually one, two, or three times per day or as necessary to control the condition. Alternatively, the drug-oligomer conjugates may be administered by continuous infusion. The duration of treatment depends on the type of insulin deficiency being treated and may be for as long as the life of the subject.

In another aspect of the present invention, a method of providing a pharmaceutical composition comprises selecting an amount of a bile salt to include in the composition based on the ability of the bile salt to increase the solubility of a fatty acid component when the composition has a pH of 8.5 or less.

According to other embodiments of the present invention, a method of providing a pharmaceutical composition comprises selecting an amount of a fatty acid to include in the composition based on the ability of the fatty acid to lower the precipitation point of a bile salt component in the composition to a pH of 5.5 or less.

According to still other embodiments of the present invention, a method of providing a pharmaceutical composition comprises selecting an amount of a fatty acid to include in the composition based on the ability of the fatty acid to alter the precipitation characteristics of a bile salt component in the composition.

The present invention will now be described with reference to the following examples. It should be appreciated that these examples are for the purposes of illustrating aspects of the present invention, and do not limit the scope of the invention as defined by the claims.

EXAMPLES

Example 1

Synthesis of 6-(2-{2-[2-(2-{2-[2-(2-methoxyethoxy)ethoxy]-ethoxy}-ethoxy)-ethoxy]-ethoxy}-ethoxy)-hexanoic Acid 2,5-dioxo-pyrrolidin-1-yl Ester (8)

Hexaethylene glycol monobenzyl ether (1). An aqueous sodium hydroxide solution prepared by dissolving 3.99 g (100 mmol) NaOH in 4 ml water was added slowly to monodispersed hexaethylene glycol (28.175 g, 25 ml, 100 mmol). Benzyl chloride (3.9 g, 30.8 mmol, 3.54 ml) was added and the reaction mixture was heated with stirring to 100° C. for 18 hours. The reaction mixture was then cooled, diluted with brine (250 ml) and extracted with methylene chloride (200 ml×2). The combined organic layers were washed with brine once, dried over $Na_2SO_4$, filtered and concentrated in vacuo to a dark brown oil. The crude product mixture was purified via flash chromatography (silica gel, gradient elution: ethyl acetate to 9/1 ethyl acetate/methanol) to yield 8.099 g (70%) of monodispersed compound 1 as a yellow oil.

Ethyl 6-methylsulfonyloxyhexanoate (2). A solution of monodispersed ethyl 6-hydroxyhexanoate (50.76 ml, 50.41 g, 227 mmol) in dry dichloromethane (75 ml) was chilled in an ice bath and placed under a nitrogen atmosphere. Triethylamine (34.43 ml, 24.99 g, 247 mmol) was added. A solution of methanesulfonyl chloride (19.15 ml, 28.3 g, 247 mmol) in dry dichloromethane (75 ml) was added dropwise from an addition funnel. The mixture was stirred for three and one half hours, slowly being allowed to come to room temperature as the ice bath melted. The mixture was filtered through silica gel, and the filtrate was washed successively with water, saturated $NaHCO_3$, water and brine. The organics were dried over $Na_2SO_4$, filtered and concentrated in vacuo to a pale yellow oil. Final purification of the crude product was achieved by flash chromatography (silica gel, 1/1 hexanes/ethyl acetate) to give the monodispersed compound 2 (46.13 g, 85%) as a clear, colorless oil. FAB MS: m/e 239 (M+H), 193 (M-$C_2H_5O$).

6-{2-[2-(2-{2-[2-(2-Benzyloxyethoxy)ethoxy]ethoxy}-ethoxy)-ethoxy]-ethoxy}-hexanoic acid ethyl ester (3). Sodium hydride (3.225 g or a 60% oil dispersion, 80.6 mmol) was suspended in 80 ml of anhydrous toluene, placed under a nitrogen atmosphere and cooled in an ice bath. A solution of the monodispersed alcohol 9 (27.3 g, 73.3 mmol) in 80 ml dry toluene was added to the NaH suspension. The mixture was stirred at 0° C. for thirty minutes, allowed to come to room temperature and stirred for another five hours, during which time the mixture became a clear brown solution. The monodispersed mesylate 10 (19.21 g, 80.6 mmol) in 80 ml dry toluene was added to the NaH/alcohol mixture, and the combined solutions were stirred at room temperature for three days. The reaction mixture was quenched with 50 ml methanol and filtered through basic alumina. The filtrate was concentrated in vacuo and purified by flash chromatography (silica gel, gradient elution: 3/1 ethyl acetate/hexanes to ethyl acetate) to yield the monodispersed compound 3 as a pale yellow oil (16.52 g, 44%). FAB MS: m/e 515 (M+H).

6-{2-[2-(2-{2-[2-(2-hydroxyethoxy)ethoxy]ethoxy}-ethoxy)-ethoxy]-ethoxy}-hexanoic acid ethyl ester (4). Substantially monodispersed benzyl ether 3 (1.03 g, 2.0 mmol) was dissolved in 25 ml ethanol. To this solution was added 270 mg 10% Pd/C, and the mixture was placed under a hydrogen atmosphere and stirred for four hours, at which time TLC showed the complete disappearance of the starting material. The reaction mixture was filtered through Celite 545 to remove the catalyst, and the filtrate was concentrated in vacuo to yield the monodispersed compound 4 as a clear oil (0.67 g, 79%). FAB MS: m/e 425 (M+H), 447 (M+Na).

6-{2-[2-(2-{2-[2-(2-methylsulfonylethoxy)ethoxy]ethoxy}-ethoxy)-ethoxy]-ethoxy}-hexanoic acid ethyl ester (5). The monodispersed alcohol 4 (0.835 g, 1.97 mmol) was dissolved in 3.5 ml dry dichloromethane and placed under a nitrogen atmosphere. Triethylamine (0.301 ml, 0.219 g, 2.16 mmol) was added and the mixture was chilled in an ice bath. After two minutes, the methanesulfonyl chloride (0.16 ml, 0.248 g, 2.16 mmol) was added. The mixture was stirred for 15 minutes at 0° C., then at room temperature for two hours. The reaction mixture was filtered through silica gel to remove the triethylammonium chloride, and the filtrate was washed successively with water, saturated $NaHCO_3$, water and brine. The organics were dried over $Na_2SO_4$, filtered and concentrated in vacuo. The residue was purified by column chromatography (silica gel, 9/1 ethyl acetate/methanol) to give monodispersed compound 5 as a clear oil (0.819 g, 83%). FAB MS: m/e 503 (M+H).

6-(2-{2-[2-(2-{2-[2-(2-methoxyethoxy)ethoxy]-ethoxy}-ethoxy)-ethoxy]-ethoxy}-ethoxy)-hexanoic acid ethyl ester (6). NaH (88 mg of a 60% dispersion in oil, 2.2 mmol) was suspended in anhydrous toluene (3 ml) under $N_2$ and chilled to 0° C. Monodispersed diethylene glycol monomethyl ether (0.26 ml, 0.26 g, 2.2 mmol) that had been dried via azeotropic distillation with toluene was added. The reaction mixture was allowed to warm to room temperature and stirred for four hours, during which time the cloudy grey suspension became clear and yellow and then turned brown. Mesylate 5 (0.50 g, 1.0 mmol) in 2.5 ml dry toluene was added. After stirring at room temperature over night, the reaction was quenched by the addition of 2 ml of methanol and the resultant solution was filtered through silica gel. The filtrate was concentrated in vacuo and the FAB MS: m/e 499 (M+H), 521 (M+Na). Additional purification by preparatory chromatography (silica gel, 19/3 chloroform/methanol) provided the monodispersed compound 6 as a clear yellow oil (0.302 g 57%). FAB MS: m/e 527 (M+H), 549 (M+Na).

6-(2-{2-[2-(2-{2-[2-(2-methoxyethoxy)ethoxy]-ethoxy}-ethoxy)-ethoxy]-ethoxy}-ethoxy)-hexanoic acid (7). Monodispersed ester 6 (0.25 g, 0.46 mmol) was stirred for 18 hours in 0.71 ml of 1 N NaOH. After 18 hours, the mixture was concentrated in vacuo to remove the alcohol and the residue dissolved in a further 10 ml of water. The aqueous solution was acidified to pH 2 with 2 N HCl and the product was extracted into dichloromethane (30 ml×2). The combined organics were then washed with brine (25 ml×2), dried over $Na_2SO_4$, filtered and concentrated in vacuo to yield the monodispersed compound 15 as a yellow oil (0.147 g, 62%). FAB MS: m/e 499 (M+H), 521 (M+Na).

6-(2-{2-[2-(2-{2-[2-(2-methoxyethoxy)ethoxy]-ethoxy}-ethoxy)-ethoxy]-ethoxy}-ethoxy)-hexanoic acid 2,5-dioxo-pyrrolidin-1-yl ester (8). Monodispersed acid 7 (0.209 g, 0.42 mmol) was dissolved in 4 ml of dry dichloromethane and added to a dry flask already containing NHS(N-hydroxysuccinimide) (57.8 mg, 0.502 mmol) and EDC (1-(3-dimethylaminopropyl)-3-ethylcarbodiimide hydrochloride) (98.0 mg, 0.502 mmol) under a $N_2$ atmosphere. The solution was stirred at room temperature overnight and filtered through silica gel to remove excess reagents and the urea formed from the EDC. The filtrate was concentrated in vacuo to provide the activated monodispersed oligomer 8 as a dark yellow oil (0.235 g, 94%). FAB MS: m/e 596 (M+H), 618 (M+Na).

Example 2

Synthesis of Activated $MPEG_7$-$C_8$ (14)

Mesylate of triethylene glycol monomethyl ether (9). To a solution of $CH_2Cl_2$ (100 mL) cooled to 0° C. in an ice bath was added monodispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL $CH_2Cl_2$). The reaction mixture was stirred for 30 min at 0° C., allowed to warm to room temperature, and then stirred for 2 h. The crude reaction mixture was filtered through Celite (washed $CH_2Cl_2$~200 mL), then washed with $H_2O$ (300 mL), 5% $NaHCO_3$ (300 mL), $H_2O$ (300 mL), sat. NaCl (300 mL), dried $MgSO_4$, and evaporated to dryness. The oil was then placed on a vacuum line for ~2 h to ensure dryness and afforded the monodispersed compound 9 as a yellow oil (29.15 g, 80% yield).

Heptaethylene glycol monomethyl ether (10). To a solution of monodispersed tetraethylene glycol (51.5 g, 0.27 mol) in THF (1L) was added potassium t-butoxide (14.8 g, 0.13 mol, small portions over ~30 min). The reaction mixture was then stirred for 1 h and then 9 (29.15 g, 0.12 mol) dissolved in THF (90 mL) was added dropwise and the reaction mixture was stirred overnight. The crude reaction mixture was filtered through Celite (washed $CH_2Cl_2$, ~200 mL) and evaporated to dryness. The oil was then dissolved in HCl (250 mL, 1 N) and washed with ethyl acetate (250 mL) to remove excess 9. Additional washings of ethyl acetate (125 mL) may be-required to remove remaining 9. The aqueous phase was washed repetitively with $CH_2Cl_2$ (125 mL volumes) until most of the compound 18 has been removed from the aqueous phase. The first extraction will contain 9, 10, and dicoupled side product and should be back extracted with HCl (125 mL, 1N). The organic layers were combined and evaporated to dryness. The resultant oil was then dissolved in $CH_2Cl_2$ (100 mL) and washed repetitively with $H_2O$ (50 mL volumes) until 10 was removed. The aqueous fractions were combined, total volume 500 mL, and NaCl was added until the solution became cloudy and then was washed with $CH_2Cl_2$ (2×500 mL). The organic layers were combined, dried $MgSO_4$, and evaporated to dryness to afford the monodispersed compound 10 as an oil (16.9 g, 41% yield). It may be desirable to repeat one or more steps of the purification procedure to ensure high purity.

8-Bromooctoanate (11). To a solution of monodispersed 8-bromooctanoic acid (5.0 g, 22 mmol) in ethanol (100 mL) was added $H_2SO_4$ (0.36 mL, 7.5 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford a clear oil 11 (5.5 g, 98% yield).

$MPEG_7$-$C_8$ ester (12). To a solution of the monodispersed compound 10 (3.0 g, 8.8 mmol) in ether (90 mL) was added potassium t-butoxide (1.2 g, 9.6 mmol) and the reaction mixture was stirred for 1 h. Then dropwise addition of the monodispersed compound 11 (2.4 g, 9.6 mmol), dissolved in ether (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, and evaporated to dryness. Column chromatography (Silica, ethyl acetate to ethyl acetate/methanol, 10:1) was performed and afforded the monodispersed compound 12 as a clear oil (0.843 g, 19% yield).

$MPEG_7$-$C_8$ acid (13). To the oil of the monodispersed compound 12 (0.70 g, 1.4 mmol) was added 1N NaOH (2.0 mL) and the reaction mixture was stirred for 4 h. The crude reaction mixture was concentrated, acidified (pH~2), saturated with NaCl, and washed $CH_2Cl_2$ (2×50 mL). The organic layers were combined, washed sat. NaCl, dried $MgSO_4$, and evaporated to dryness to afford the monodispersed compound 13 as a clear oil (0.35 g, 53% yield).

Activation of $MPEG_7$-$C_8$ acid. Monodispersed mPEG7-C8-acid 13 (0.31 g, 0.64 mmol) was dissolved in 3 ml of anhydrous methylene chloride and then solution of N-hydroxysuccinimide (0.079 g, 0.69 mmol) and EDCI.HCl (135.6 mg, 0.71 mmol) in anhydrous methylene chloride added. Reaction was stirred for several hours, then washed with 1N HCl, water, dried over $MgSO_4$, filtered and concentrated. Crude material was purified by column chromatography, concentrated to afford monodispersed activated $MPEG_7$-$C_8$ 14 as a clear oil and dried via vacuum.

Example 3

Synthesis of Activated $MPEG_7$-$C_{10}$ (19)

10-hydroxydecanoate (15). To a solution of monodispersed 10-hydroxydecanoic acid (5.0 g, 26.5 mmol) in ethanol (100 mL) was added $H_2SO_4$ (0.43 mL, 8.8 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford the monodispersed compound 15 as a clear oil (6.9 g, 98% yield).

Mesylate of 10-hydroxydecanoate (16). To a solution of $CH_2Cl_2$ (27 mL) was added monodispersed 10-hydroxydecanoate 15 (5.6 g, 26 mmol) and cooled to 0° C. in an ice bath. Then triethylamine (5 mL, 37 mmol) was added and the reaction mixture was stirred for 15 min at 0° C. Then methanesulfonyl chloride (2.7 mL, 24 mmol) dissolved in $CH_2Cl_2$ (3 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), dried $MgSO_4$, and evaporated to dryness to afford the monodispersed compound 16 as a yellowish oil (7.42 g, 97% yield).

$MPEG_7$-$C_{10}$ Ester (17). To a solution of substantially monodispersed heptaethylene glycol monomethyl ether 10 (2.5 g, 7.3 mmol) in tetrahydrofuran (100 mL) was added sodium hydride (0.194 g, 8.1 mmol) and the reaction mixture was stirred for 1 h. Then dropwise addition of mesylate of monodispersed 10-hydroxydecanoate 16 (2.4 g, 8.1 mmol), dissolved in tetrahydrofuran (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, evaporated to dryness, chromatographed (silica, ethyl acetate/methanol, 10:1), and chromatographed (silica, ethyl acetate) to afford the monodispersed compound 17 as a clear oil (0.570 g, 15% yield).

$MPEG_7$-$C_{10}$ Acid (18). To the oil of monodispersed $mPEG_7$-$C_{10}$ ester 17 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the monodispersed compound 18 as a clear oil (0.340 g, 62% yield).

Activation of $MPEG_7$-$C_{10}$ Acid. The monodispersed acid 18 was activated using procedures similar to those described above in Example 10 to provide activated $MPEG_7$-$C_{10}$ Oligomer 19.

Example 4

Synthesis of Activated $C_{18}(PEG_6)$ Oliomer (22)

Synthesis of $C_{18}(PEG_6)$ Oligomer (20). Monodispersed stearoyl chloride (0.7 g, 2.31 mmol) was added slowly to a mixture of monodispersed $PEG_6$ (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over $MgSO_4$, concentrated and dried via vacuum. Purified monodispersed compound 20 was analyzed by FABMS: m/e 549/M+H.

Activation of $C_{18}(PEG_6)$ Oligomer. Activation of monodispersed $C_{18}(PEG_6)$ oligomer was accomplished in two steps:

1) Monodispersed stearoyl-$PEG_6$ 20 (0.8 g, 1.46 mmol) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining substantially monodispersed stearoyl PEG6 chloroformate 21 was dried over $P_2O_5$ overnight.

2) To a solution of monodispersed stearoyl-$PEG_6$ chloroformate 21 (0.78 g, 1.27 mmol) and TEA (128 mg, 1.27 mmol) in anhydrous-methylene chloride, N-hydroxy succinimide (NHS) solution in methylene chloride was added. The reaction mixture was stirred for 16 hours, then washed with water, dried over $MgSO_4$, filtered, concentrated and dried via vacuum to provide the monodispersed activated $C_{18}(PEG_6)$ oligomer 22.

Example 51

Synthesis of Activated $C_{18}(PEG_8)$ Oligomer (28)

Tetraethylene glycol monobenzylether (23). To the oil of monodispersed tetraethylene glycol (19.4 g, 0.10 mol) was added a solution of NaOH (4.0 g in 4.0 mL) and the reaction was stirred for 15 mm. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed $CH_2Cl_2$ (2×200 mL). The organic layers were combined, washed sat. NaCl, dried $MgSO_4$, and chromatographed (silica, ethyl acetate) to afford the monodispersed compound 23 as a yellow oil (6.21 g, 71% yield).

Mesylate of tetraethylene glycol monobenzylether (24). To a solution of $CH_2Cl_2$ (20 mL) was added monodispersed tetraethylene glycol monobenzylether 23 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in $CH_2Cl_2$ (2 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), and dried $MgSO_4$. The resulting yellow oil was chromatographed on a pad of silica containing activated carbon (10 g) to afford the monodispersed compound 24 as a clear oil (7.10 g, 89% yield).

Octaethylene glycol monobenzylether (25). To a solution of tetrahydrofuran (140 mL) containing sodium hydride (0.43 g, 18 mmol) was added dropwise a solution of monodispersed tetraethylene glycol (3.5 g, 18 mmol) in tetrahydrofuran (10 mL) and the reaction mixture was stirred for 1 h. Then mesylate of monodispersed tetraethylene glycol monobenzylether 24 (6.0 g, 16.5 mmol) dissolved in tetrahydrofuran (10 mL) was added dropwise and the reaction mixture was stirred overnight. The crude reaction mixture was filtered through Celite (washed; $CH_2Cl_2$, 250 mL) and the filtrate was washed $H_2O$, dried $MgSO_4$, and evaporated to dryness. The resultant oil was chromatographed (silica, ethyl acetate/methanol, 10:1) and chromatographed (silica, chloroform/methanol, 25:1) to afford the monodispersed compound 25 as a clear oil (2.62 g, 34% yield).

Synthesis of Stearate $PEG_8$-Benzyl (26). To a stirred cooled solution of monodispersed octaethylene glycol monobenzylether 25 (0.998 g, 2.07 mmol) and pyridine (163.9 mg, 2.07 mmol) was added monodispersed stearoyl chloride (627.7 mg, 2.07 mmol) in benzene. The reaction mixture was stirred overnight (18 hours). The next day the reaction mixture was washed with water, dried over $MgSO_4$, concentrated and dried via vacuum. Then the crude product was chromatographed on flash silica gel column, using 10% methanol/90% chloroform. The fractions containing the product were combined, concentrated and dried via vacuum to afford the monodispersed compound 26.

Hydrogenolysis of Stearate-PEG$_8$-Benzyl. To a methanol solution of monodispersed stearate-PEG$_8$-Bzl 26 (0.854 g 1.138 mmol) Pd/C (10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with R$_f$=0.6 collected, concentrated and dried to provide the monodispersed acid 27.

Activation of C$_{18}$(PEG$_8$) Oligomer. Two step activation of monodispersed stearate-PEG8 oligomer 27 was performed as described for stearate-PEG$_6$ in Example 4 above to provide the monodispersed activated C$_{18}$(PEG$_8$) oligomer 28.

Example 6

Synthesis of Activated Triethylene Glycol Monomethyl Oligomers

A solution of toluene containing 20% phosgene (100 ml, approximately 18.7 g, 189 mmol phosgene) was chilled to 0° C. under a N$_2$ atmosphere. Monodispersed mTEG (triethylene glycol, monomethyl ether, 7.8 g, 47.5 mmol) was dissolved in 25 mL anhydrous ethyl acetate and added to the chilled phosgene solution. The mixture was stirred for one hour at 0° C., then allowed to warm to room temperature and stirred for another two and one half hours. The remaining phosgene, ethyl acetate and toluene were removed via vacuum distillation to leave the monodispersed mTEG chloroformate as a clear oily residue.

The monodispersed nTEG chloroformate was dissolved in 50 mL of dry dichloromethane to which was added TEA (triethyleamine, 6.62 mL, 47.5 mmol) and NHS (N-hydroxysuccinimide, 5.8 g, 50.4 mmol). The mixture was stirred at room temperature under a dry atmosphere for twenty hours during which time a large amount of white precipitate appeared. The mixture was filtered to remove this precipitate and concentrated in vacuo. The resultant oil was taken up in dichloromethane and washed twice with cold deionized water, twice with 1N HCl and once with brine. The organics were dried over MgSO$_4$, filtered and concentrated to provide the monodispersed title compound as a clear, light yellow oil. If necessary, the NHS ester could be further purified by flash chromatography on silica gel using EtOAc as the elutant.

Example 7

Synthesis of Activated Palmitate-TEG Oligomers

Monodispersed palmitic anhydride (5 g; 10 mmol) was dissolved in dry THF (20 mL) and stirred at room temperature. To the stirring solution, 3 mol excess of pyridine was added followed by monodispersed triethylene glycol (1.4 mL). The reaction mixture was stirred for 1 hour (progress of the reaction was monitored by TLC; ethyl acetate-chloroform; 3:7). At the end of the reaction, THF was removed and the product was mixed with 10% H$_2$SO$_4$ acid and extracted ethyl acetate (3×30 mL). The combined extract was washed sequentially with water, brine, dried over MgSO$_4$, and evaporated to give monodispersed palmitate-TEG oligomers.

A solution of N,N'-disuccinimidyl carbonate (3 mmol) in DMF (~10 mL) is added to a solution of the monodispersed palmitate-TEG oligomers (1 mmol) in 10 mL of anydrous DMF while stirring. Sodium hydride (3 mmol) is added slowly to the reaction mixture. The reaction mixture is stirred for several hours (e.g., 5 hours). Diethyl ether is added to precipitate the monodispersed activated title oligomer. This process is repeated 3 times and the product is finally dried.

Example 8

Synthesis of Activated Hexaethylene Glycol Monomethyl Oligomers

Monodispersed activated hexaethylene glycol monomethyl ether was prepared analogously to that of monodispersed triethylene glycol in Example 6 above. A 20% phosgene in toluene solution (35 mL, 6.66 g, 67.4 mmol phosgene) was chilled under a N$_2$ atmosphere in an ice/salt water bath. Monodispersed hexaethylene glycol (1.85 mL, 2.0 g, 6.74 mmol) was dissolved in 5 mL anhydrous EtOAc and added to the phosgene solution via syringe. The reaction mixture was kept stirring in the ice bath for one hour, removed and stirred a further 2.5 hours at room temperature. The phosgene, EtOAc, and toluene were removed by vacuum distillation, leaving monodispersed methyl hexaethylene glycol chloroformate as a clear, oily residue.

The monodispersed chloroformate was dissolved in 20 mL dry dichloromethane and placed under a dry, inert atmosphere. Triethylamine (0.94 mL, 0.68 g, 6.7 mmol) and then NHS(N-hydroxy succinimide, 0.82 g, 7.1 mmol) were added, and the reaction mixture was stirred at room temperature for 18 hours. The mixture was filtered through silica gel to remove the white precipitate and concentrated in vacuo. The residue was taken up in dichloromethane and washed twice with cold water, twice with 1 N HCl and once with brine. The organics were dried over Na$_2$SO$_4$, filtered and concentrated. Final purification was done via flash chromatography (silica gel, EtOAc) to obtain the activated monodispersed hexaethylene monomethyl ether.

Example 9

Synthesis of Avtivated Heptaethylene Glycol Monomethyl Ether

8-Methoxy-1-(methylsulfonyl)oxy-3,6-dioxaoctane (29). A solution of monodispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC (CHCl$_3$ with 15% MeOH as the elutant) showed no remaining triethylene glycol monomethyl ether.

The reaction mixture was diluted with another 75 mL of dichloromethane and washed successively with saturated NaHCO$_3$, water and brine. The organics were dried over Na$_2$SO$_4$, filtered and concentrated in vacuo to give a monodispersed mixture of compounds 29 as a clear oil (5.31 g, 86%).

Heptaethylene glycol mono methyl ether (30). To a stirred solution of monodispersed tetraethylene glycol (35.7 mmol) in dry DMF (25.7 mL), under N$_2$ was added in portion a 60% dispersion of NaH in mineral oil, and the mixture was stirred at room temperature for 1 hour. To the resulting sodium salt of the tetraethylene glycol was added a solution of monodispersed mesylate 29 (23.36) in dry DMF (4 ml) in a single portion, and the mixture was stirred at room temperature for 3.5 hours. Progress of the reaction was monitored by TLC (12% $CH_3OH$—$CHCl_3$). The reaction mixture was diluted with an equal amount of 1N HCl, and extracted with ethyl acetate (2×20 ml) and discarded. Extraction of aqueous solution and work-up gave monodispersed heptaethylene glycol monomethyl ether 30 (82–84% yield). Oil; Rf 0.46 (methanol:chloroform=3:22); MS m/z calc'd for $C_{15}H_{32}O_8$ 340.21 ($M^++1$), found 341.2.

Activation of heptaethylene glycol monomethyl ether. Monodispersed heptaethylene glycol monomethyl ether 30 is activated by a procedure similar to that used in Example 6 above to activate triethylene glycol monomethyl ether to provide the activated heptaethylene glycol monomethyl ether.

Example 10

Synthesis of Activated Decaethylene Glycol Monomethyl Ether (33)

20-methoxy-1-(methylsulfonyl)oxy-3,6,9,12,15,18-hexaoxaeicosane (31). Monodispersed compound 31 was obtained in quantitative yield from compound 30 and methanesulfonyl chloride as described for 29 in Example 9 above, as an oil; Rf 0.4 (ethyl acetate:acetonitrile=1:5); MS m/z calc'd for $C_{17}H_{37}O_{10}$ 433.21 ($M^++1$), found 433.469.

Decaethylene glycol monomethyl ether (32). Monodispersed compound 32 was prepared from compound 31 and monodispersed triethylene glycol using the procedure described above in Example 17. Oil; Rf 0.41 (methanol:chloroform=6:10); MS m/z calc'd for $C_{21}H_{44}O_{11}$ 472.29 ($M^++1$), found 472.29.

Activation of decaethylene glycol mono methyl ether. Monodispersed decaethylene glycol monomethyl ether 32 is activated by a procedure similar to that used in Example 6 above to activate triethylene glycol monomethyl ether to provide the activated decaethylene glycol monomethyl ether 33.

Example 11

HIM2 Oral Liquid Process

A general procedure to manufacture an oral liquid pharmaceutical composition of the present invention is shown below: The process involves making a premix without the drug, filtering the premix, then adding the premix and drug solution together.

Quantitative Composition of HIM2 Oral Liquid, 6 mg/mL

| Excipient | Composition | | Quantity per Batch |
|---|---|---|---|
| | % w/v | mg/mL | (g) |
| HIM2 | 0.6 | 6 | 6.0[1] |
| Sodium Cholate | 3.0 | 30 | 30.0 |
| Oleic Acid, NF | 1.0 | 10 | 10.0 |
| Sucralose, 25% | 0.8 | 8 | 8.0 |
| Strawberry Flavor | 0.4 | 4 | 4.0 |
| Capric Acid | 0.5 | 5 | 5.0 |
| Lauric Acid | 0.5 | 5 | 5.0 |
| Citric Acid Anhydrous, USP | 6.72 | 67.2 | 67.2 |
| Trolamine, NF | 5.22 | 52.2 | 52.2 |
| Tromethamine, USP | 4.24 | 42.4 | 42.4 |
| Sodium Hydroxide, NF | 1.88 | 18.8 | 18.8 |
| Sodium Hydroxide, 5 N | QS | QS | QS |
| Hydrochloric Acid, 5 N | QS | QS | QS |
| Sterile Water for Irrigation, USP | QS | QS | QS |
| Total | 100% | 1.0 mL | 1077.4 g |

[1]Weight adjusted for protein content.

Preparation of Premix for HIM2 Oral Liquid
1. Add 94.3% of the tromethamine and the trolamine, citric acid and sodium hydroxide (NF) to 350 g sterile water for irrigation and stir until completely dissolved.
2. Moderately heat and maintain the temperature through steps 3 & 4, below.
3. Add the sodium cholate to step 2 and stir until dissolved.
4. Add the oleic acid, capric acid, lauric acid, sucralose solution and strawberry flavor to step 3 and stir until dissolved.
5. Adjust the temperature to approximately room temperature.
6. Adjust the pH of step 5, if necessary, to 7.8±0.1 using 5N sodium hydroxide or 5N hydrochloric acid.
7. QS to the pre-mix batch weight with sterile water for irrigation.
8. Filter the step 7 product.

Preparation of HIM2 Oral Liquid, 6 mg/mL
1. Dispense the required quantity of the Premix for HIM2 Oral Liquid and continue stirring while performing steps 2 through 4 below.
2. Add the remaining tromethamine to 140 g of the sterile water for irrigation and stir until dissolved.
3. Adjust the pH of step 2, if necessary, to 7.7±0.2 using 5N sodium hydroxide or 5N hydrochloric acid.
4. Filter the step 3 liquid.
5. Add all of the HIM2 to step 4. and stir until completely dissolved.
6. Add all of step 5 to step 1 and stir.
7. Adjust the temperature to approximately room temperature, if necessary
8. Adjust the pH of step 7, if necessary, to 7.6–7.9 using 5N sodium hydroxide or 5N hydrochloric acid.

Example 12

HIM2 Oral Tablet Process

A general procedure to manufacture an oral tablet formulation of the present invention is shown below: The process involves making a lyophilized powder, adding tableting excipients and compressing.

Quantitative Composition of HIM2 Oral Tablets, 10 mg

| Excipient | Quantity per Batch (g) |
|---|---|
| Lyo Portion | |
| HIM2 | 2.50[1] |
| Sodium Cholate | 30.0 |

-continued

| Excipient | Quantity per Batch (g) |
|---|---|
| Oleic Acid, NF | 10.0 |
| Sucralose, 25% | 8.0 |
| Strawberry Flavor | 4.0 |
| Capric Acid | 5.0 |
| Lauric Acid | 5.0 |
| Citric Acid Anhydrous, USP | 67.2 |
| Trolamine, NF | 52.2 |
| Tromethamine, USP | 42.4 |
| Sodium Hydroxide, NF | 18.8 |
| Sodium Hydroxide, 5 N | QS |
| Hydrochloric Acid, 5 N | QS |
| Sterile Water for Irrigation, USP | QS |
| Total | 1077.4g |
| Tablet Portion | |
| Lyo Portion | 127.6 |
| Citric Acid | 29.7 |
| Sodium Citrate dihydrate | 84.2 |
| Tris Base (tris(hydroxymethyl)aminomethane) | 106.7 |
| Microcrystilline Cellulose | 24.8 |
| Explotab | 9.4 |
| Total | 382.3 |

[1]Weight adjusted for protein content.

Procedure:
1. Dispense the required ingredients with the exception of the Sterile Water for Irrigation, USP,
2. Dispense 1500 g of Sterile Water for Irrigation, USP, and add to the processing vessel above.
3. Add the following ingredients to step 2 and mix until dissolved completely:
   a. all of the Sodium Cholate
   b. all of the Dibasic Sodium Phosphate Heptahydrate, USP
4. Add the following ingredients to step 3 and mix vigorously.
   a. All of the Capric Acid
   b. All of the Lauric Acid
   c. All of the Sodium Hydroxide, NF (Note: Heat will be generated by the addition of Sodium Hydroxide, NF.)
5. Adjust the step 4 solution to a temperature between 45° C. and 50° C., and mix until a clear solution results.
6. Cool to room temperature and, if necessary, adjust the step 5 pH to 7.2–7.8 using Sodium Hydroxide, 1N, or Hydrochloric Acid, 1N.
7. Add all of the HIM2 PEG 7 to step 6 and mix vigorously until a clear solution results.
8. Determine the amount of additional Sterile Water for Irrigation, USP, to add (if necessary)
9. Lyophilize this solution until a white amorphous powder results.
10. Blend the lyo portion with the tableting excipients.
11. Compress on a tablet press to achieve desired size, shape and hardness.

Example 13

Liquid oral pharmaceutical compositons formulated in accordance with Example 11 above were administered to male CF-1 mice (~20–25 g). The animals were fasted overnight and deprived of food during the experiment. Water was provided ad libitum. The mice were maintained in cages with 5 animals per cage and kept in a room with a 12:12 L:D cycle (6:00 a.m.-6:00 p.m.). The mice were tested in groups of 5 animals per dose. Each group of mice (N=5) received either insulin conjugate-075, insulin conjucate-076, insulin-conjugate-084, insulin-conjugate-098, insulin-conjugate-101, insulin conjugate-106 or HIM2 orally at 1.25 and 2.5 mg/kg.

Figure 7:
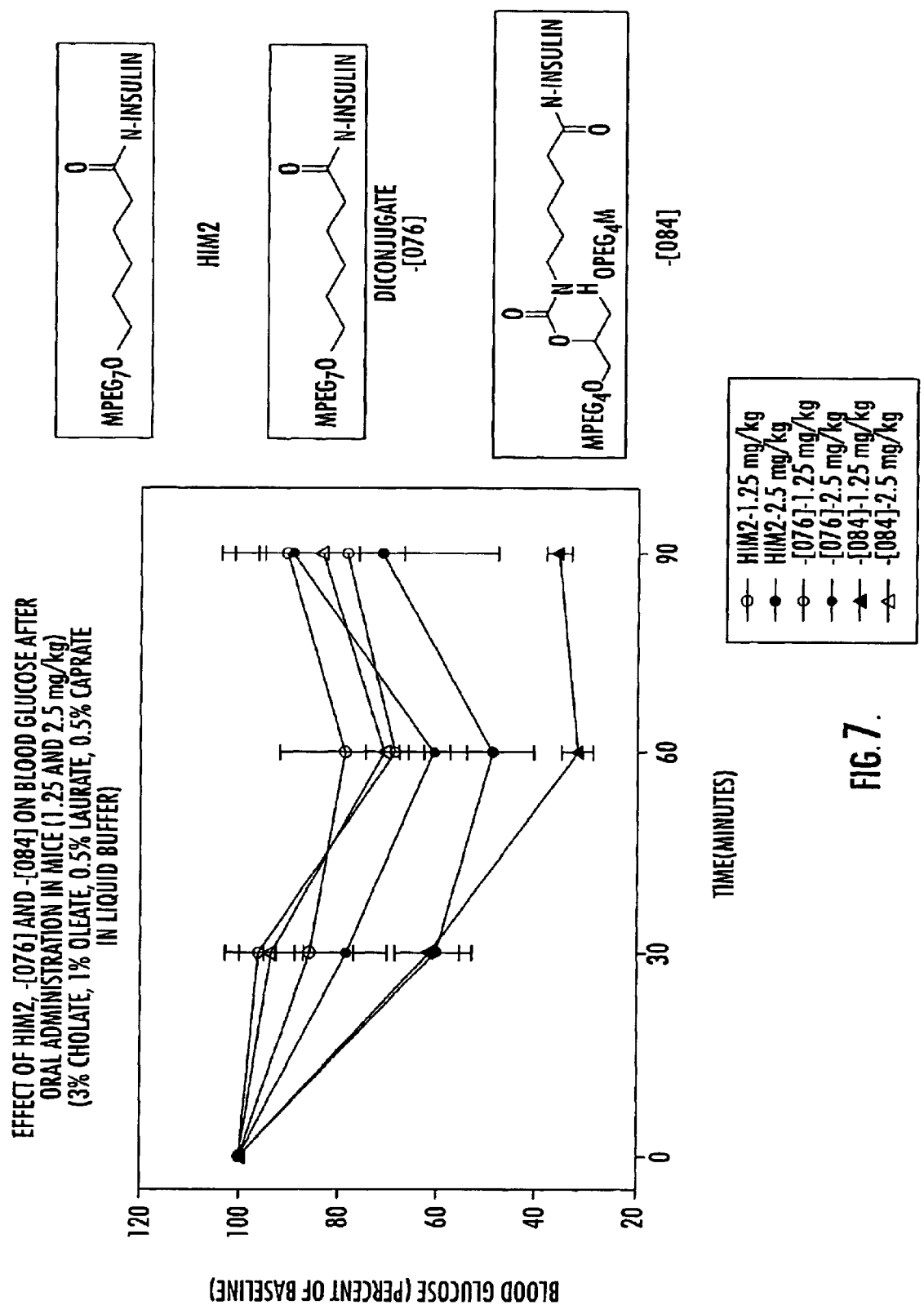
FIG. 7 illustrates a blood glucose vs. time curve resulting from oral administration of embodiments of the present invention in mice.
Figure 8:
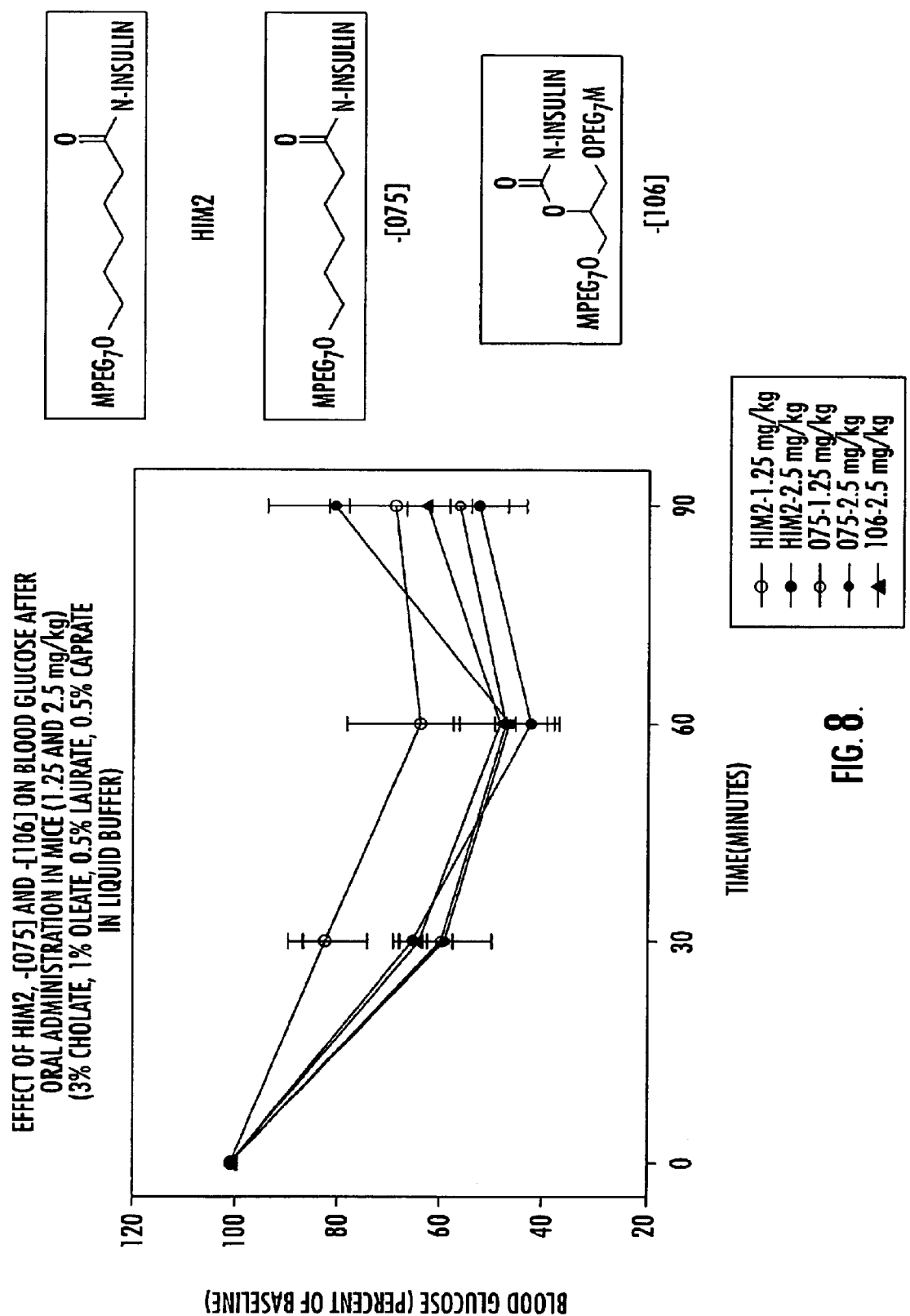
FIG. 8 illustrates a blood glucose vs. time curve resulting from oral administration of embodiments of the present invention in mice.
Figure 9:
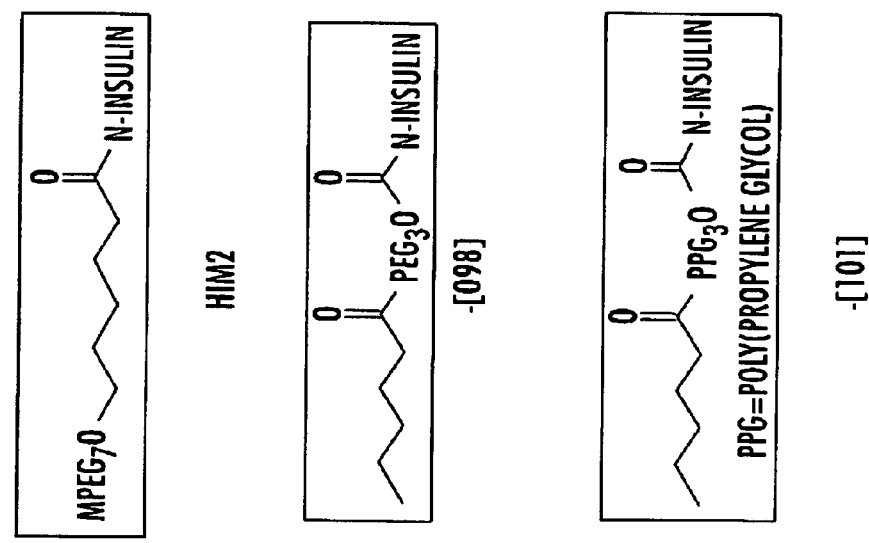
FIG. 9 illustrates a blood glucose vs. time curve resulting from oral administration of embodiments of the present invention in mice.
Figure 9:
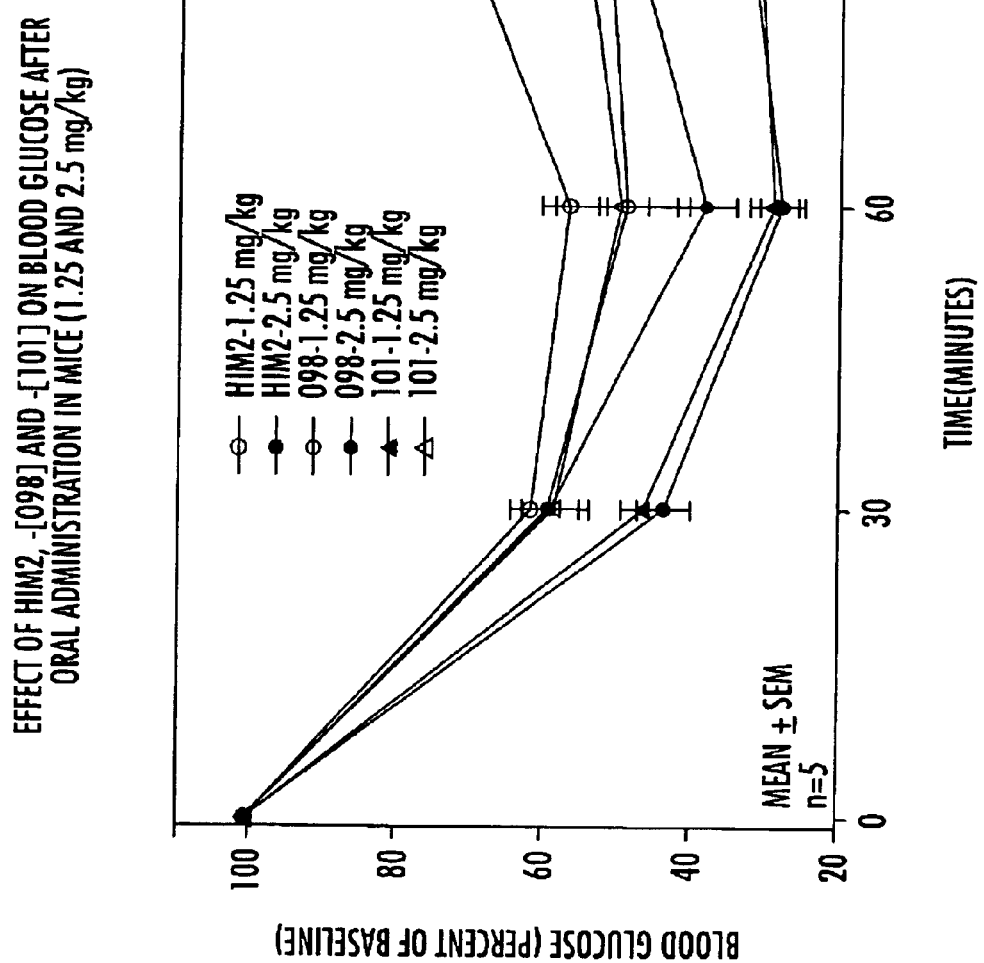

The insulin conjugates and HIM2 were provided at concentrations of 0.125 and 0.25 mg/ml. The dosing volume was 10.0 mL/kg. Total doses (each compound) animals received were 1.25 and 2.5 mg/kg. Oral doses were administered using a gavaging needle (Popper gavage needle for mice #20; 5 cm from hub to bevel). Effect of the various conjugates on blood glucose level is illustrated in FIGS. 7, 8, and 9.

Example 14

Liquid oral pharmaceutical compositons formulated in accordance with Example 11 above were administered to healthy human volunteers in a 4-way crossover study both pre-prandial and post-prandial. The insulin conjugate HIM2 was provided at concentrations of 0.125. 0.25 and 0.5 mg/ml and these were compared to baseline values where no dosing occured. 20 mL oral doses were provided followed by 70 mL of water.

Figure 2:
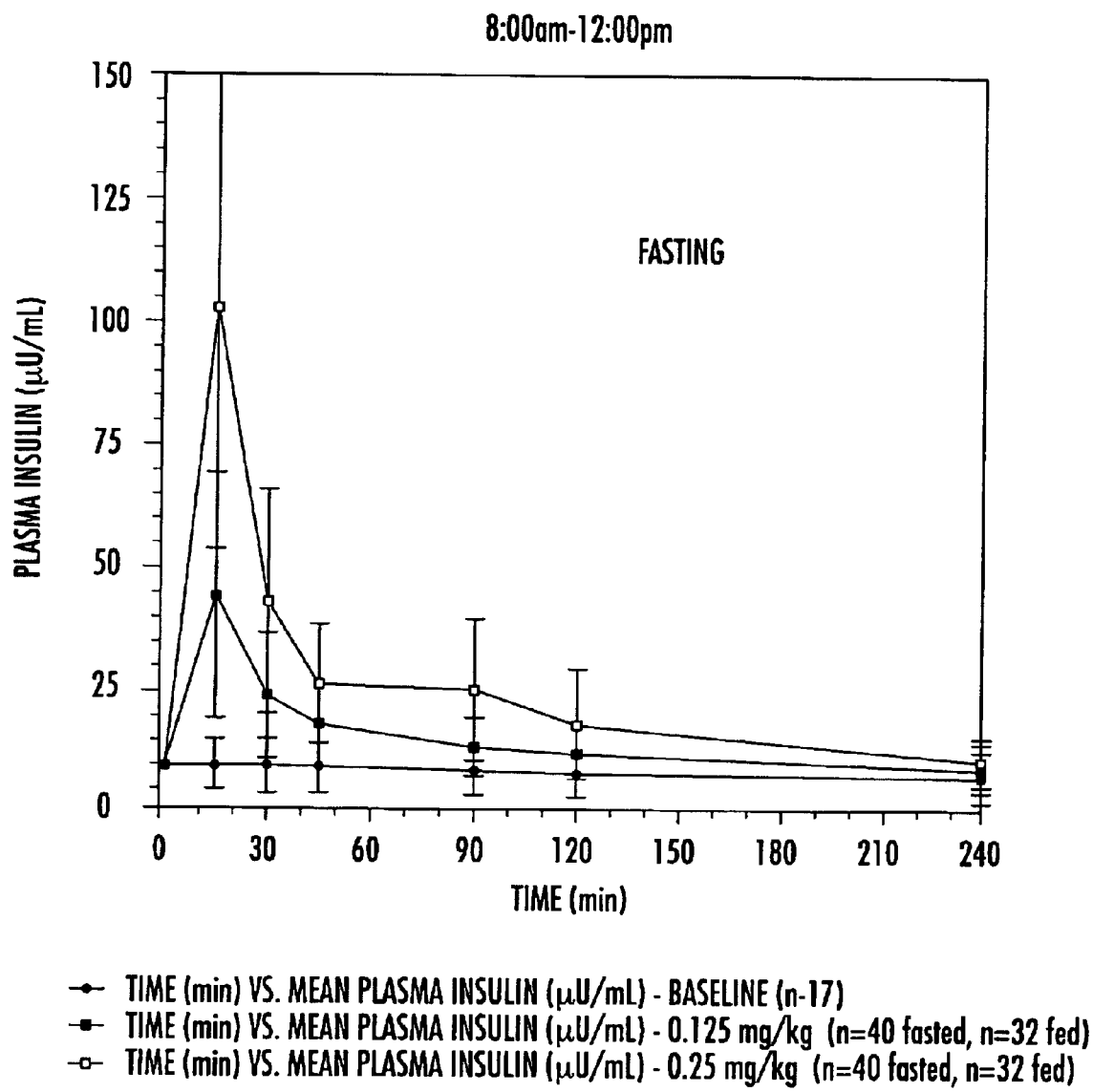
FIG. 2 illustrates a comparison of mean plasma insulin vs. time curve resulting from oral administration of various doses of embodiments of the present invention in fasting, non-diabetic subjects compared with a mean plasma insulin vs. time curve for baseline plasma insulin.
Figure 3:
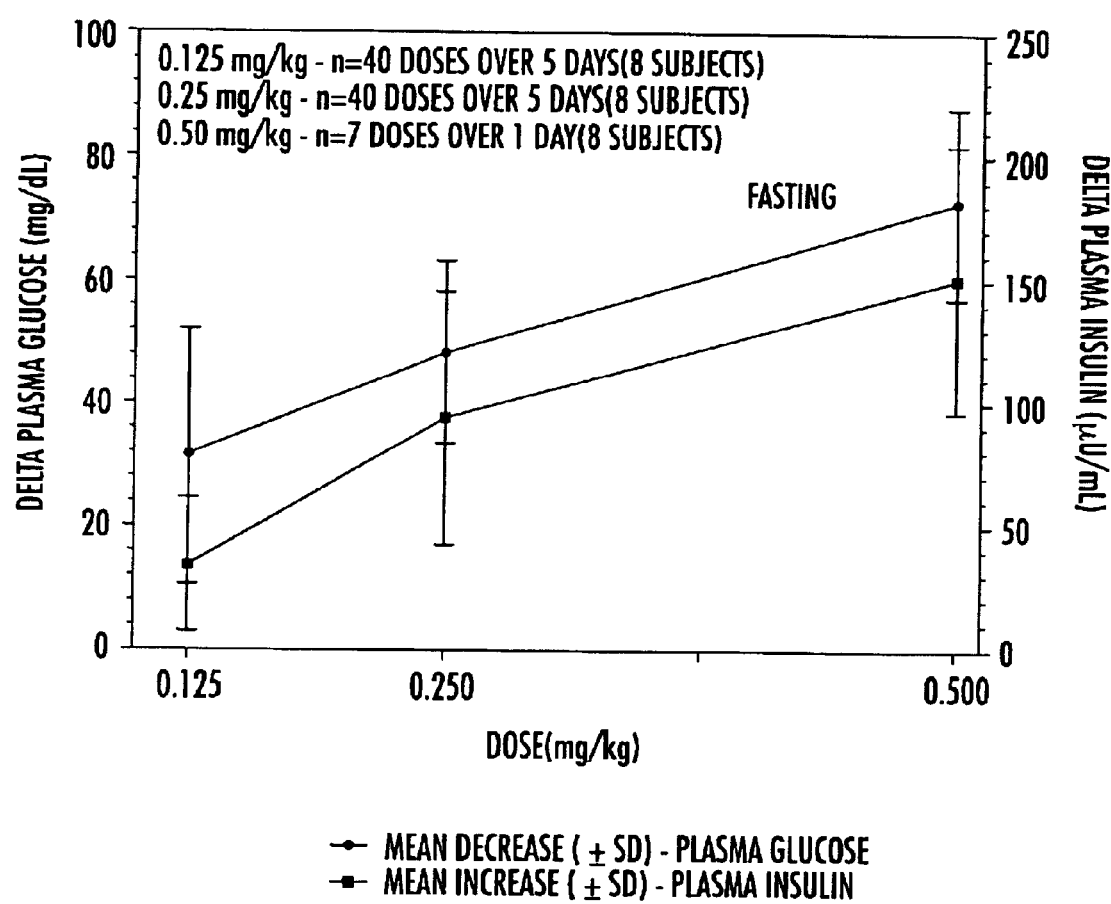
FIG. 3 illustrates glucose and insulin dose responses resulting from oral administration of embodiments of the present invention in fasting, non-diabetic subjects.

For the pre-prandial phase (fasted), subjects were fasted overnight and a single dose was administered in the morning. If blood glucose levels fell below 50 mg/dL, the subjects were rescued with a dextrose infusion. The effect of the conjugate HIM2 on blood glucose levels is illustrated in FIG. 1. HIM2 plasma levels (expressed in insulin equivalents) are shown in FIG. 2. The glucose/dose response and HIM2/dose response is shown in FIG. 3.

Figure 4:
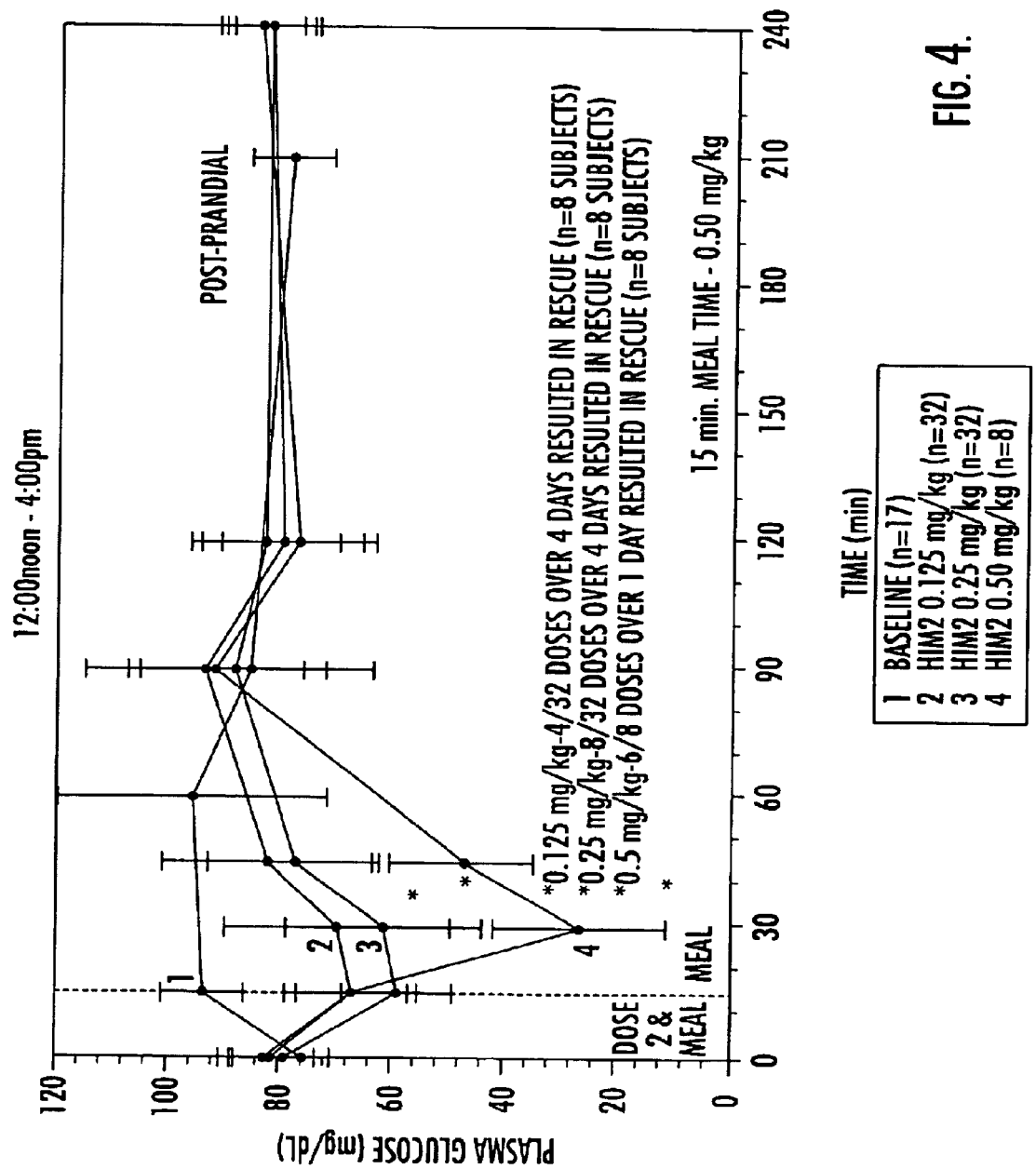
FIG. 4 illustrates a comparison of mean plasma glucose vs. time curves resulting from post-prandial, oral administration of various doses of embodiments of the present invention in non-diabetic subjects compared with a mean plasma glucose vs. time curve for baseline plasma glucose.
Figure 5:
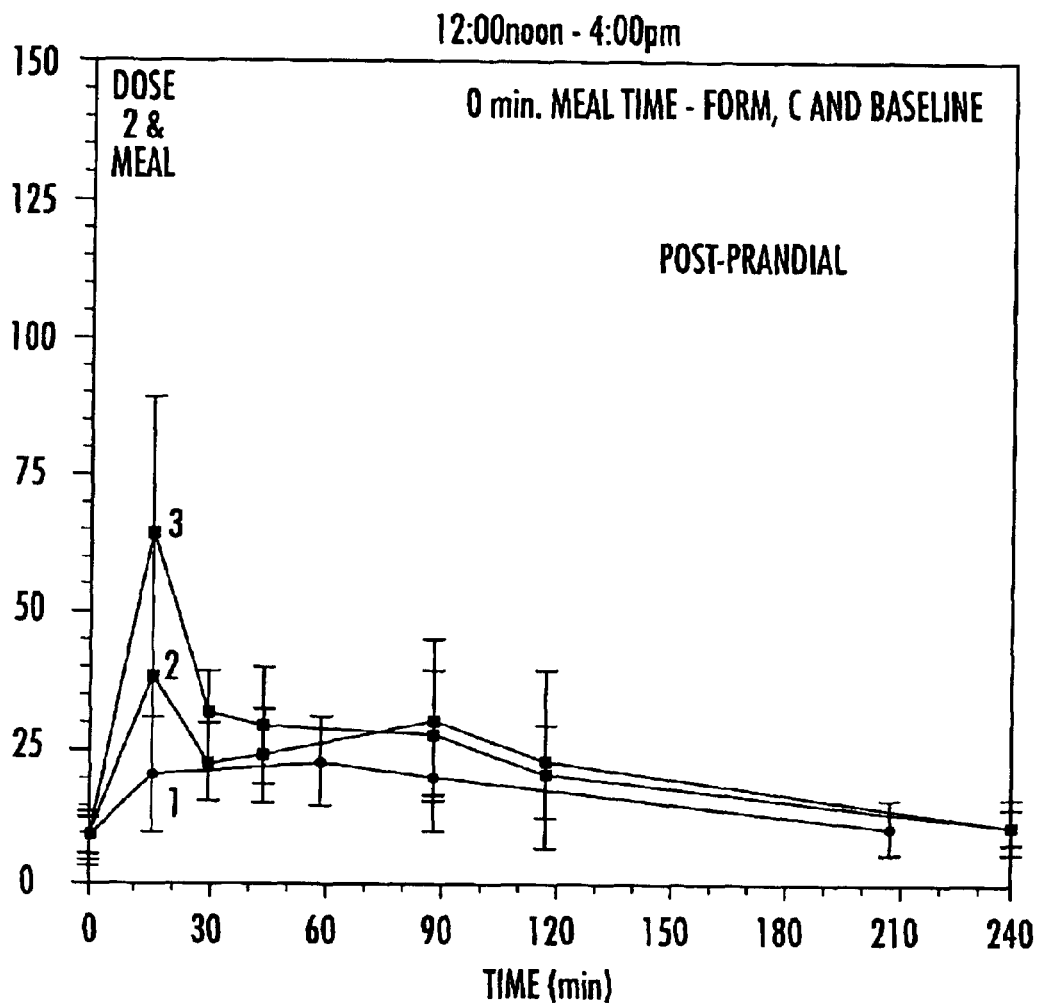
FIG. 5 illustrates a comparison of mean plasma insulin vs. time curve resulting from post-prandial, oral administration of various doses of embodiments of the present invention in non-diabetic subjects compared with a mean plasma insulin vs. time curve for baseline plasma insulin.
Figure 6:
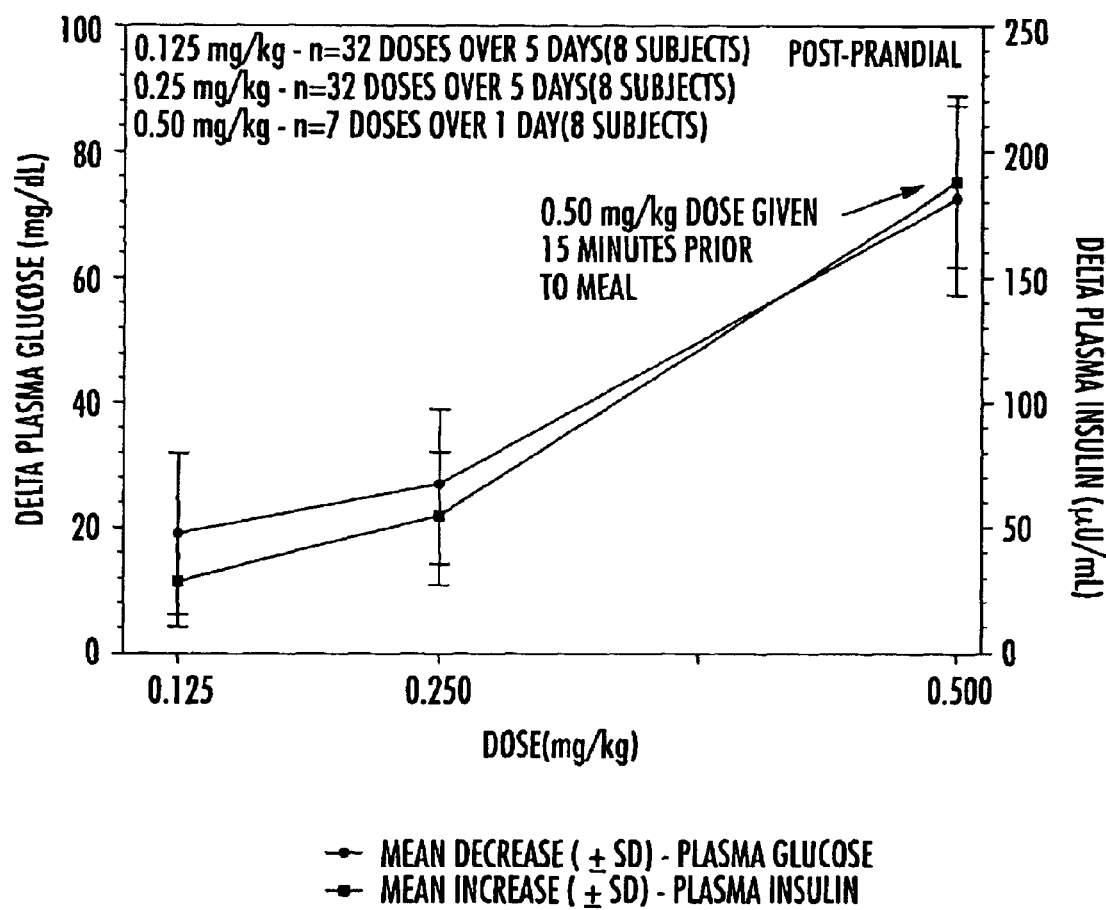
FIG. 6 illustrates glucose and insulin dose responses resulting from post-prandial oral administration of embodiments of the present invention in non-diabetic subjects.

For the post-prandial phase (fed), subjects received a single dose followed 15 minutes later by a meal. If blood glucose levels fell below 50 mg/dL, the subjects were rescued with a dextrose infusion. The effect of the conjugate HIM2 on blood glucose levels is illustrated in FIG. 4. HIM2 plasma levels (expressed in insulin equivalents) are shown in FIG. 5. The glucose/dose response and HIM2/dose response is shown in FIG. 6.

The present invention has been described herein with reference to its preferred embodiments. These embodiments do not serve to limit the invention, but are set forth for illustrative purposes. The scope of the invention is defined by the claims that follow.

That which is claimed is:

1. A pharmaceutical composition comprising:
    an insulin drug-oligomer conjugate comprising an insulin polypeptide covalently coupled to an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human;
    a fatty acid component comprising a fatty acid; and
    a bile salt component comprising a bile salt; wherein the fatty acid component and the bile salt component are present in a weight-to-weight ratio of between 1:5 and 5:1, wherein the fatty acid component is present in an amount sufficient to lower the precipitation point of the bile salt compared to a precipitation point of the bile salt if the fatty acid component were not present in the pharmaceutical composition, and wherein the bile salt component is present in an amount sufficient to lower the solubility point of the fatty acid compared to a solubility point of the fatty acid if the bile salt were not present in the pharmaceutical composition.

2. The pharmaceutical composition of claim 1, wherein the fatty acid component is present in an amount sufficient to lower the precipitation point of the bile salt by at least 1.0 pH units.

3. The pharmaceutical composition of claim 1, wherein the bile salt component is present in an amount sufficient to lower the solubility point of the fatty acid by at least 0.5 pH units.

4. The pharmaceutical composition of claim 1, wherein the bile salt component is present in an amount such that the fatty acid is soluble at a pH of 8.2, and wherein the fatty acid component is present in an amount such that the bile salt remains in solution at a pH of 5.5.

5. The pharmaceutical composition of claim 1, wherein the fatty acid component and the bile salt component are present in a weight ratio of between 1:2 and 2:1.

6. The pharmaceutical composition of claim 1, wherein the bile salt component comprises a pharmaceutically acceptable salt of cholic acid.

7. The pharmaceutical composition of claim 1, wherein the bile salt component is sodium cholate.

8. The pharmaceutical composition of claim 1, wherein the fatty acid component comprises a medium-chain fatty acid and a long-chain fatty acid.

9. The pharmaceutical composition of claim 8, wherein the medium-chain fatty acid is selected from the group consisting of lauric acid, capric acid, and mixtures thereof, and the long-chain fatty acid is oleic acid.

10. The pharmaceutical composition of claim 1, wherein the pH of the composition is between 6.2 and 9.0.

11. The pharmaceutical composition of claim 1, further comprising a buffering component.

12. The pharmaceutical composition of claim 11, wherein the buffering component comprises tris-base or trolamine.

13. The pharmaceutical composition of claim 11, wherein the pharmaceutical composition is a liquid pharmaceutical composition.

14. The pharmaceutical composition of claim 13, wherein the liquid pharmaceutical composition is suitable for oral administration.

15. The pharmaceutical composition of claim 1, wherein the pharmaceutical composition is a solid dosage pharmaceutical composition.

16. The pharmaceutical composition of claim 1, wherein the insulin analog comprises lysine at the B29 position of the insulin analog and the oligomeric moiety is coupled to the B29 lysine.

17. The pharmaceutical composition of claim 1, wherein the insulin drug-oligomer conjugate is present as a substantially monodispersed mixture.

18. The pharmaceutical composition of claim 1, wherein the insulin drug-oligomer conjugate is present as a monodispersed mixture.

19. The pharmaceutical composition of claim 1, wherein the insulin drug-oligomer conjugate is amphiphilically balanced.

20. The pharmaceutical composition of claim 1, wherein the oligomeric moiety comprises a hydrophilic moiety and a lipophilic moiety.

21. The pharmaceutical composition of claim 1, wherein the insulin drug-oligomer conjugate comprises the structure of Formula V:

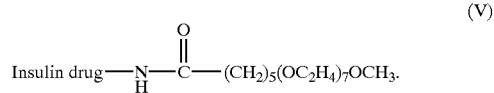

(V)

22. A pharmaceutical composition comprising:
an insulin drug-oligomer conjugate comprising an insulin polypeptide covalently coupled to an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human;
a bile salt component comprising a bile salt; and
a fatty acid component comprising a fatty acid, wherein the fatty acid component and the bile salt component are present in a weight-to-weight ratio of between 1:5 and 5:1, and wherein the fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were not present in the composition.

23. The pharmaceutical composition of claim 22, wherein the precipitation point of the bile salt is at or below a pH of 5.5.

24. The pharmaceutical composition of claim 22, wherein the first bile salt are able to re-solubilize in less than 75% of the time it would have taken for the second bile salt particles to re-solubilize.

25. The pharmaceutical composition of claim 22, wherein the fatty acid component and the bile salt component are present in a weight ratio of between 1:2 and 2:1.

26. The pharmaceutical composition of claim 22, wherein the bile salt component comprises a pharmaceutically acceptable salt of cholic acid.

27. The pharmaceutical composition of claim 22, wherein the bile salt component is sodium cholate.

28. The pharmaceutical composition of claim 22, wherein the fatty acid component comprises a medium-chain fatty acid and a long-chain fatty acid.

29. The pharmaceutical composition of claim 28, wherein the medium-chain fatty acid is selected from the group consisting of lauric acid, capric acid, and mixtures thereof, and the long-chain fatty acid is oleic acid.

30. The pharmaceutical composition of claim 22, wherein the pH of the composition is between 6.2 and 9.0.

31. The pharmaceutical composition of claim 22, further comprising a buffering component.

32. The pharmaceutical composition of claim 31, wherein the buffering component comprises tris-base or trolamine.

33. The pharmaceutical composition of claim 31, wherein the pharmaceutical composition is a liquid pharmaceutical composition.

34. The pharmaceutical composition of claim 33, wherein the liquid pharmaceutical composition is suitable for oral administration.

35. The pharmaceutical composition of claim 33, wherein the liquid pharmaceutical composition is suitable for parenteral administration.

36. The pharmaceutical composition of claim 22, wherein the pharmaceutical composition is a solid dosage pharmaceutical composition.

37. The pharmaceutical composition of claim 22, wherein the insulin analog comprises lysine at the B29 position of the insulin analog and the oligomeric moiety is coupled to the B29 lysine.

38. The pharmaceutical composition of claim 22, wherein the insulin drug-oligomer conjugate is present as a substantially monodispersed mixture.

39. The pharmaceutical composition of claim 22, wherein the insulin drug-oligomer conjugate is present as a monodispersed mixture.

40. The pharmaceutical composition of claim 22, wherein the insulin drug-oligomer conjugate is amphiphilically balanced.

41. The pharmaceutical composition of claim 22, wherein the oligomeric moiety comprises a hydrophilic moiety and a lipophilic moiety.

42. The pharmaceutical composition of claim 22, wherein the insulin drug-oligomer conjugate comprises the structure of Formula V:

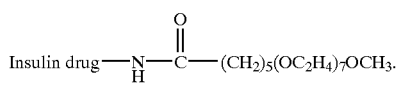
(V)

43. A pharmaceutical composition comprising:
an insulin drug-oligomer conjugate comprising an insulin polypeptide and an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human;
between 0.1 and 15% (w/v) of a fatty acid component; wherein the fatty acid component comprises a medium-chain fatty acid and a long-chain fatty acid; and
between 0.1 and 15% (w/v) of a bile salt component;
wherein the fatty acid component and the bile salt component are present in a weight-to-weight ratio of between 1:5 and 5:1.

44. The pharmaceutical composition of claim 43, wherein the fatty acid component and the bile salt component are present in a weight ratio of between 1:2 and 2:1.

45. The pharmaceutical composition of claim 43, wherein the bile salt component comprises a pharmaceutically acceptable salt of cholic acid.

46. The pharmaceutical composition of claim 43, wherein the bile salt component is sodium cholate.

47. The pharmaceutical composition of claim 43, wherein the medium-chain fatty acid is selected from the group consisting of lauric acid, capric acid, and mixtures thereof, and the long-chain fatty acid is oleic acid.

48. The pharmaceutical composition of claim 43, wherein the pH of the composition is between 6.2 and 9.0.

49. The pharmaceutical composition of claim 43, further comprising a buffering component.

50. The pharmaceutical composition of claim 49, wherein the buffering component comprises tris-base or trolamine.

51. The pharmaceutical composition of claim 49, wherein the pharmaceutical composition is a liquid pharmaceutical composition.

52. The pharmaceutical composition of claim 51, wherein the liquid pharmaceutical composition is suitable for oral administration.

53. The pharmaceutical composition of claim 51, wherein the liquid pharmaceutical composition is suitable for parenteral administration.

54. The pharmaceutical composition of claim 43, wherein the pharmaceutical composition is a solid dosage pharmaceutical composition.

55. The pharmaceutical composition of claim 43, wherein the insulin analog comprises lysine at the B29 position of the insulin analog and the oligomeric moiety is coupled to the B29 lysine.

56. The pharmaceutical composition of claim 43, wherein the insulin drug-oligomer conjugate is present as a substantially monodispersed mixture.

57. The pharmaceutical composition of claim 43, wherein the insulin drug-oligomer conjugate is present as a monodispersed mixture.

58. The pharmaceutical composition of claim 43, wherein the insulin drug-oligomer conjugate is amphiphilically balanced.

59. The pharmaceutical composition of claim 43, wherein the oligomeric moiety comprises a hydrophilic moiety and a lipophilic moiety.

60. The pharmaceutical composition of claim 43, wherein the insulin drug-oligomer conjugate comprises the structure of Formula V:

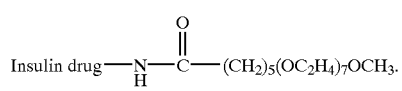
(V)

61. A pharmaceutical composition comprising:
an insulin drug-oligomer conjugate comprising the structure of Formula V:

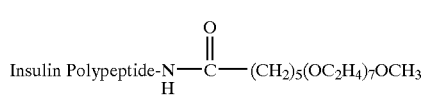
(V)

wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human and the oligomeric moiety of the conjugate is coupled to the B29 lysine of the insulin polypeptide;
between 0.1 and 15% (w/v) of a fatty acid component comprising capric acid, lauric acid, and oleic acid; and between 0.1 and 15% (w/v) of a bile salt component comprising a pharmaceutically acceptable salt of cholic acid;

wherein the fatty acid component and the bile salt component are present in a weight-to-weight ratio of between 1:5 and 5:1.

62. A method of treating an insulin deficiency in a subject in need of such treatment, said method comprising administering to the subject a pharmaceutical composition comprising (a) a therapeutically effective amount of an insulin drug-oligomer conjugate that comprises an insulin polypeptide covalently coupled to an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human;

(b) a fatty acid component comprising a fatty acid; and (c) a bile salt component comprising a bile salt, wherein the fatty acid component and the bile salt component are present in a weight ratio of between 1:5 and 5:1, wherein the fatty acid component is present in an amount sufficient to lower the precipitation point of the bile salt compared to a precipitation point of the bile salt if the fatty acid component were not present in the pharmaceutical composition, and wherein the fatty acid component is present in an amount sufficient to lower the solubility point of the fatty acid compared to a solubility point of the fatty acid if the bile salt were not present in the pharmaceutical composition.

63. The method of claim 62, wherein the fatty acid component is present in an amount sufficient to lower the precipitation point of the bile salt by at least 1.0 pH units.

64. The method of claim 62, wherein the bile salt component is present in an amount sufficient to lower the solubility point of the fatty acid by at least 0.5 pH units.

65. The method of claim 62, wherein the bile salt component is present in an amount such that the fatty acid is soluble at a pH of 8.2, and wherein the fatty acid component is present in an amount such that the bile salt remains in solution at a pH of 5.5.

66. The method of claim 62, wherein the fatty acid component and the bile salt component are present in a weight ratio of between 1:2 and 2:1.

67. The method of claim 62, wherein the bile salt component comprises a pharmaceutically acceptable salt of cholic acid.

68. The method of claim 62, wherein the bile salt component is sodium cholate.

69. The method of claim 62, wherein the fatty acid component comprises a medium-chain fatty acid and a long-chain fatty acid.

70. The method of claim 69, wherein the medium-chain fatty acid is selected from the group consisting of lauric acid, capric acid, and mixtures thereof, and the long-chain fatty acid is oleic acid.

71. The method of claim 62, wherein the pH of the composition is between 6.2 and 9.0.

72. The method of claim 62, further comprising a buffering component.

73. The method of claim 72, wherein the buffering component comprises tris-base or trolamine.

74. The method of claim 72, wherein the pharmaceutical composition is a liquid pharmaceutical composition.

75. The method of claim 62, wherein the pharmaceutical composition is a solid dosage pharmaceutical composition.

76. The method of claim 62, wherein the method comprises orally administering the pharmaceutical composition to the subject.

77. The method of claim 62, wherein the insulin analog comprises lysine at the B29 position of the insulin analog and the oligomeric moiety is coupled to the B29 lysine.

78. The method of claim 62, wherein the insulin drug-oligomer conjugate is present as a substantially monodispersed mixture.

79. The method of claim 62, wherein the insulin drug-oligomer conjugate is present as a monodispersed mixture.

80. The method of claim 62, wherein the insulin drug-oligomer conjugate is amphiphilically balanced.

81. The method of claim 62, wherein the oligomeric moiety comprises a hydrophilic moiety and a lipophilic moiety.

82. The method of claim 62, wherein the insulin drug-oligomer conjugate comprises the structure of Formula V:

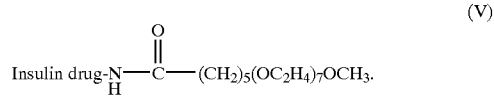

(V)

83. A method of treating an insulin deficiency in a subject in need of such treatment, said method comprising administering to the subject a pharmaceutical composition comprising:

(a) a therapeutically effective amount of an insulin drug-oligomer conjugate that comprises an insulin polypeptide covalently coupled to an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human;

(b) a bile salt component comprising a bile salt; and (c) a fatty acid component comprising a fatty acid, wherein the fatty acid component and the bile salt component are present in a weight ratio of between 1:5 and 5:1, and wherein the fatty acid component is present in a first amount such that, at the precipitation point of the bile salt, the bile salt precipitates as first bile salt particles that, upon a return to a pH above the precipitation point of the bile salt, re-solubilize more quickly than second bile salt particles that would have precipitated if the fatty acid component were not present in the composition.

84. The method of claim 83, wherein the precipitation point of the bile salt is at or below a pH of 5.5.

85. The method of claim 83, wherein the first bile salt are able to re-solubilize in less than 75% of the time it would have taken for the second bile salt particles to re-solubilize.

86. The method of claim 83, wherein the fatty acid component and the bile salt component are present in a weight ratio of between 1:2 and 2:1.

87. The method of claim 83, wherein the bile salt component comprises a pharmaceutically acceptable salt of cholic acid.

88. The method of claim 83, wherein the bile salt component is sodium cholate.

89. The method of claim 83, wherein the fatty acid component comprises a medium-chain fatty acid and a long-chain fatty acid.

90. The method of claim 89, wherein the medium-chain fatty acid is selected from the group consisting of lauric acid, capric acid, and mixtures thereof, and the long-chain fatty acid is oleic acid.

91. The method of claim 83, wherein the pH of the composition is between 6.2 and 9.0.

92. The method of claim 83, further comprising a buffering component.

93. The method of claim 92, wherein the buffering component comprises tris-base or trolamine.

94. The method of claim 83, wherein the pharmaceutical composition is a liquid pharmaceutical composition.

95. The method of claim 83, wherein the pharmaceutical composition is a solid dosage pharmaceutical composition.

96. The method of claim 83, wherein the method comprises orally administering the pharmaceutical composition to the subject.

97. The method of claim 83, wherein the insulin analog comprises lysine at the B29 position of the insulin analog and the oligomeric moiety is coupled to the B29 lysine.

98. The method of claim 83, wherein the insulin drug-oligomer conjugate is present as a substantially monodispersed mixture.

99. The method of claim 83, wherein the insulin drug-oligomer conjugate is present as a monodispersed mixture.

100. The method of claim 83, wherein the insulin drug-oligomer conjugate is amphiphilically balanced.

101. The method of claim 83, wherein the oligomeric moiety comprises a hydrophilic moiety and a lipophilic moiety.

102. The method of claim 83, wherein the insulin drug-oligomer conjugate comprises the structure of Formula V:

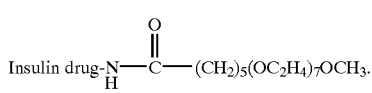
(V)

103. A method of treating an insulin deficiency in a subject in need of such treatment, said method comprising administering to the subject a pharmaceutical composition comprising:
(a) a therapeutically effective amount of an insulin drug-oligomer conjugate that comprises an insulin polypeptide and an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human; $Val^{B28}$ $Pro^{B29}$ insulin, human; and $Ala^{B28}$ $Pro^{B29}$ insulin, human; (b) between 0.1 and 15% (w/v) of a fatty acid component comprises a medium-chain fatty acid and a long-chain fatty acid; and
(c) between 0.1 and 15% (w/v) of a bile salt component, wherein the fatty acid component and the bile salt component are present in a weight to weight ratio of between 1:5 and 5:1.

104. The method of claim 103, wherein the fatty acid component and the bile salt component are present in a weight ratio of between 1:2 and 2:1.

105. The method of claim 103, wherein the bile salt component comprises a pharmaceutically acceptable salt of cholic acid.

106. The method of claim 103, wherein the bile salt component is sodium cholate.

107. The method of claim 103, wherein the medium-chain fatty acid is selected from the group consisting of lauric acid, capric acid, and mixtures thereof, and the long-chain fatty acid is oleic acid.

108. The method of claim 103, wherein the pH of the composition is between 6.2 and 9.0.

109. The method of claim 103, further comprising a buffering component.

110. The method of claim 109, wherein the buffering component comprises tris-base or trolamine.

111. The method of claim 109, wherein the pharmaceutical composition is a liquid pharmaceutical composition.

112. The method of claim 103, wherein the pharmaceutical composition is a solid dosage pharmaceutical composition.

113. The method of claim 103, wherein the method comprises orally administering the pharmaceutical composition to the subject.

114. The method of claim 103, wherein the insulin analog comprises lysine at the B29 position of the insulin analog and the oligomeric moiety is coupled to the B29 lysine.

115. The method of claim 103, wherein the insulin drug-oligomer conjugate is present as a substantially monodispersed mixture.

116. The method of claim 103, wherein the insulin drug-oligomer conjugate is present as a monodispersed mixture.

117. The method of claim 103, wherein the insulin drug-oligomer conjugate is amphiphilically balanced.

118. The method of claim 103, wherein the oligomeric moiety comprises a hydrophilic moiety and a lipophilic moiety.

119. The method of claim 103, wherein the insulin drug-oligomer conjugate comprises the structure of Formula V:

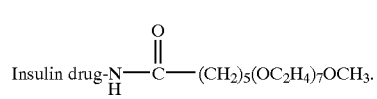
(V)

120. A pharmaceutical composition comprising:
an insulin drug-oligomer conjugate comprising an insulin polypeptide and an oligomeric moiety, wherein the insulin polypeptide is an insulin analog selected from the group consisting of $Gly^{A21}$ insulin, human; $Gly^{A21}$ $Gln^{B3}$ insulin, human; $Ala^{A21}$ insulin, human; $Ala^{A21}$ $Gln^{B3}$ insulin, human; $Gln^{B3}$ insulin, human; $Gln^{B30}$ insulin, human; $Gly^{A21}$ $Glu^{B30}$ insulin, human; $Gly^{A21}$ $Gln^{B3}$ $Glu^{B30}$ insulin, human; $Gln^{B3}$ $Glu^{B30}$ insulin, human; $Asp^{B28}$ insulin, human; $Lys^{B28}$ insulin, human; $Leu^{B28}$ insulin, human; $Val^{B28}$ insulin, human; $Ala^{B28}$ insulin, human; $Asp^{B28}$ $Pro^{B29}$ insulin, human; $Lys^{B28}$ $Pro^{B29}$ insulin, human; $Leu^{B28}$ $Pro^{B29}$ insulin, human;

Val$^{B28}$ Pro$^{B29}$ insulin, human; and Ala$^{B28}$ Pro$^{B29}$ insulin, human;

between 0.1 and 15% (w/v) of a fatty acid component; and between 0.1 and 15% (w/v) of a bile salt component;

wherein the fatty acid component and the bile salt component are present in a weight-to-weight ratio of between 1:5 and 5:1, and wherein the pharmaceutical composition comprises a buffering component that comprises tris-base or trolamine.

121. The pharmaceutical composition of claim 120, wherein the pharmaceutical composition is a liquid pharmaceutical composition suitable for oral administration.

122. The pharmaceutical composition of claim 120, wherein the pharmaceutical composition is a liquid pharmaceutical composition suitable for parenteral administration.

123. The pharmaceutical composition of claim 120, wherein the pharmaceutical composition is a solid dosage pharmaceutical composition.

124. A pharmaceutical composition comprising:

an insulin drug-oligomer conjugate comprising an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

between 0.1 and 15% (w/v) of a fatty acid component; and between 0.1 and 15% (w/v) of a bile salt component;

wherein the fatty acid component and the bile salt component are present in a weight-to-weight ratio of between 1:5 and 5:1, and wherein the insulin drug-oligomer conjugate is present as a monodispersed mixture.

125. A pharmaceutical composition comprising:

an insulin drug-oligomer conjugate comprising an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

between 0.1 and 15% (w/v) of a fatty acid component; and between 0.1 and 15% (w/v) of a bile salt component;

wherein the fatty acid component and the bile salt component are present in a weight-to-weight ratio of between 1:5 and 5:1, and wherein the insulin drug-oligomer conjugate is present as a monodispersed mixture.

126. A pharmaceutical composition comprising:

an insulin drug-oligomer conjugate comprising an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

between 0.1 and 15% (w/v) of a fatty acid component; and between 0.1 and 15% (w/v) of a bile salt component;

wherein the fatty acid component and the bile salt component are present in a weight-to-weight ratio of between 1:5 and 5:1, and wherein the insulin drug-oligomer conjugate comprises the structure of Formula V:

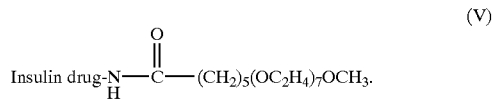

$$\text{Insulin drug-N}\underset{H}{-}\overset{\overset{O}{\|}}{C}-(CH_2)_5(OC_2H_4)_7OCH_3. \quad (V)$$

127. A method of treating an insulin deficiency in a subject in need of such treatment, said method comprising administering to the subject a pharmaceutical composition comprising: (a) a therapeutically effective amount of an insulin drug-oligomer conjugate that comprises an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

between 0.1 and 15% (w/v) of a fatty acid component; and (c) between 0.1 and 15% (w/v) of a bile salt component, wherein the fatty acid component and the bile salt component are present in a weight to weight ratio of between 1:5 and 5:1, and wherein the pharmaceutical composition comprises a buffering component that comprises tris-base or trolamine.

128. The method of claim 127, wherein the pharmaceutical composition is a liquid pharmaceutical composition suitable for oral administration.

129. The method of claim 127, wherein the pharmaceutical composition is a liquid pharmaceutical composition suitable for parenteral administration.

130. The method of claim 127, wherein the pharmaceutical composition is a solid dosage pharmaceutical composition.

131. A method of treating an insulin deficiency in a subject in need of such treatment, said method comprising administering to the subject a pharmaceutical composition comprising:

(a) a therapeutically effective amount of an insulin drug-oligomer conjugate that comprises an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

(b) between 0.1 and 15% (w/v) of a fatty acid component; and (c) between 0.1 and 15% (w/v) of a bile salt component, wherein the fatty acid component and the bile salt component are present in a weight-to-weight ratio of between 1:5 and 5:1, and wherein the insulin drug-oligomer conjugate is present as a substantially monodispersed mixture.

132. A method of treating an insulin deficiency in a subject in need of such treatment, said method comprising administering to the subject a pharmaceutical composition comprising:

(a) a therapeutically effective amount of an insulin drug-oligomer conjugate that comprises an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

(b) between 0.1 and 15% (w/v) of a fatty acid component; and (c) between 0.1 and 15% (w/v) of a bile salt component, wherein the fatty acid component and the bile salt component are present in a weight-to-weight ratio of between 1:5 and 5:1, and wherein the insulin drug-oligomer conjugate is present as a monodispersed mixture.

133. A method of treating an insulin deficiency in a subject in need of such treatment, said method comprising administering to the subject a pharmaceutical composition comprising:

(a) a therapeutically effective amount of an insulin drug-oligomer conjugate that comprises an insulin polypeptide and an oligomeric moiety, wherein the insulin polypeptide is an insulin analog selected from the group consisting of Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human; and Ala$^{B28}$ Pro$^{B29}$ insulin, human;

(b) between 0.1 and 15% (w/v) of a fatty acid component; and (c) between 0.1 and 15% (w/v) of a bile salt component, wherein the fatty acid component and the bile salt component are present in a weight to weight ratio of between 1:5 and 5:1, and wherein the insulin drug-oligomer conjugate comprises the structure of Formula V:

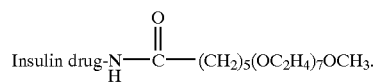

* * * * *